(12) United States Patent
Ovaa et al.

(10) Patent No.: US 8,729,009 B2
(45) Date of Patent: May 20, 2014

(54) LYSINE COMPOUNDS AND THEIR USE IN SITE- AND CHEMOSELECTIVE MODIFICATION OF PEPTIDES AND PROTEINS

(75) Inventors: Huib Ovaa, Amsterdam (NL); Farid El Oualid, Amsterdam (NL)

(73) Assignee: Stichting Het Nederlands Kanker Instituut, Amsterdam (NL)

( * ) Notice: Subject to any disclaimer, the term of this patent is extended or adjusted under 35 U.S.C. 154(b) by 165 days.

(21) Appl. No.: 13/320,686

(22) PCT Filed: May 12, 2010

(86) PCT No.: PCT/NL2010/050277
§ 371 (c)(1),
(2), (4) Date: Feb. 1, 2012

(87) PCT Pub. No.: WO2010/131962
PCT Pub. Date: Nov. 18, 2010

(65) Prior Publication Data
US 2012/0135913 A1 May 31, 2012

Related U.S. Application Data

(60) Provisional application No. 61/178,616, filed on May 15, 2009.

(30) Foreign Application Priority Data

May 15, 2009 (EP) ..................................... 09160430

(51) Int. Cl.
*A61K 38/02* (2006.01)
*C07K 2/00* (2006.01)
*C07C 319/24* (2006.01)
*C12P 21/00* (2006.01)
*G01N 21/00* (2006.01)
*C07C 323/60* (2006.01)
*C07K 1/06* (2006.01)

(52) U.S. Cl.
CPC ...................................... *A61K 38/02* (2013.01)
USPC ............ 514/1.1; 560/148; 530/300; 530/336; 435/68; 436/172

(58) Field of Classification Search
None
See application file for complete search history.

(56) References Cited

U.S. PATENT DOCUMENTS 3,637,837 A * 1/1972 Fujimoto ..................... 562/556

FOREIGN PATENT DOCUMENTS

| DE | 19 31 198 A1 | 1/1970 |
|---|---|---|
| WO | WO 99/26963 A1 | 6/1999 |
| WO | WO 2007/049803 A1 | 5/2007 |
| WO | WO 2008/137165 | 11/2008 |
| WO | WO 2008/137165 A1 | 11/2008 |

OTHER PUBLICATIONS

Geurink et al ("A General Chemical Ligation Approach Towards Isopeptide-Linked Ubiquitin and Ubiquitin-Like Assay Reagents" (2012) Chem Bio Chem 13: 293-297).*
Van Swieten et al ("Biorthogonal organic chemistry in living cells: novel strategies for labeling biomolecules" (Nov. 29, 2004) Org Biomol Chem 3: 20-27).*
Wang et al ("A Biosynthetic Route to Dehydroalanine-Containing Proteins" (2007) Angew. Chem. Int. Ed. 46: 6849-6851).*
Yan et al ("Synthesis of Peptides and Proteins without Cysteine Residues by Native Chemical Ligation Combined with Desulfurization" (2001) J Am Chem Soc 123: 526-533).*
Pickart ("Mechanisms Underlying Ubiquitination" (2001) Annu. Rev. Biochem 70: 503-533).*
Dent et al "9-BBN: An Amino Acid Protecting Group for Functionalization of Amino Acid Side Chains in Organic Solvents" (Mar. 21, 2002) Organic Letters 4(8): 1249-1251).*
Thermoscientific, "Peptide Synthesis" downloaded Jul. 10, 2013 from http://www.piercenet.com/browse.cfm?fldID=0A155590-C023-01E0-FB62-238BB9C7270F.*
Filippov, et al.. "Parallel solid phase synthesis of tricomponent bisubstrate analogues as potential fucosyltransferase inhibitors", Synlett, 5:773-778 (Jan. 2004).
Hillaert, et al., "Receptor-mediated targeting of Cathepsins in professional antigen presenting cells", Angewandte Chemie International Edition, 48:1629-1632 (Jan. 2009).
Van Swieten, et al., "Bioorthognal organic chemistry in living cells: novel strategies for labeling biomolecules", Organic & Biomolecular Chemistry, 3:20-27 (Jan. 2005).

* cited by examiner

*Primary Examiner* — Karlheinz R Skowronek
*Assistant Examiner* — Mindy Newman
(74) *Attorney, Agent, or Firm* — Browdy and Neimark, PLLC

(57) ABSTRACT

The present invention concerns new thiolysine and selenolysine compounds that can be used as building blocks for peptides and proteins, providing ligation handles for site- and chemoselective modification of said peptides and proteins. In particular, the invention provides. In particular, the invention provides (the use of) the compounds 5-thiolysine (also referred to as δ-thiolysine); 4-thiolysine (also referred to as γ-thiolysine); 5-selenolysine (also referred to as δ-selenolysine) and 4-selenolysine (also referred to as γ-selenolysine). The positioning of the thiol or selenol group at the respective carbon atom allows for a very efficient intramolecular transfer reaction to take place after conjugation with a selected ligand, and the thiol or selenol group may subsequently be removed using reported procedures, thereby restoring the native lysine structure, or be used as an additional conjugation handle. The methodology is fast and gives well-defined material.

17 Claims, 6 Drawing Sheets

Fig 1
| Band No. | Apparent Molecular Weight |
|---|---|
| 1 | 181.8 kDa |
| 2 | 115.5 kDa |
| 3 | 82.2 kDa |
| 4 | 64.2 kDa* |
| 5 | 48.8 kDa |
| 6 | 37.1 kDa |
| 7 | 25.9 kDa |
| 8 | 19.4 kDa |
| 9 | 14.8 kDa |
| 10 | 6.0 kDa |
*Orientation band (pink in color)
Fig 2
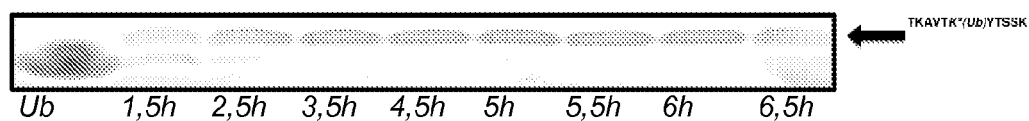
Ub    1,5h    2,5h    3,5h    4,5h    5h    5,5h    6h    6,5h
Fig 3
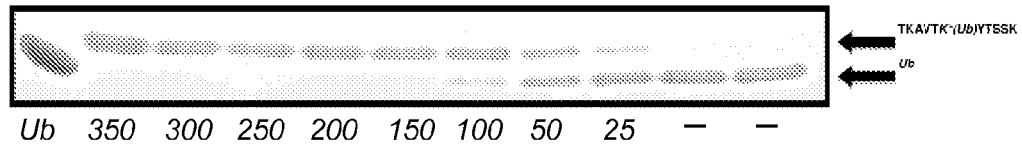
Ub    350    300    250    200    150    100    50    25    —    —
Fig 4
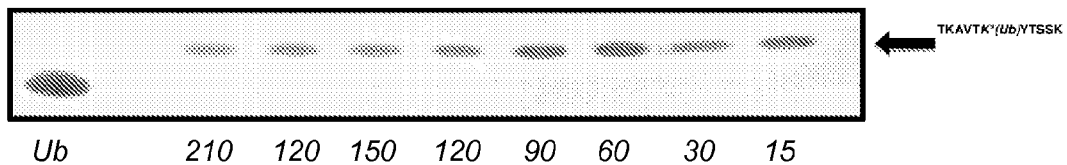
Ub          210    120    150    120    90    60    30    15

M  Ub  1  2  3  4  5  6  7  8  9

M  Ub  10  11  12  13  14  15  16

M  Ub  17  18  19  20  21  22

LYSINE COMPOUNDS AND THEIR USE IN SITE- AND CHEMOSELECTIVE MODIFICATION OF PEPTIDES AND PROTEINS

FIELD OF THE INVENTION

The present invention concerns the field of site- and chemoselective modification of peptides and proteins. In particular, the invention provides new thiolysine and selenolysine compounds that can be used as building blocks for said peptides and proteins. The lysine residue thus included can subsequently serve as the target site for conjugation with a functional agent, which functional agent, typically, is then transferred to the ε or α amine of the thio- or selenolysine residue. The present invention also concerns these processes of site- and chemoselective modification of selected peptide or protein sequences as well as the intermediate and end products obtained in the respective steps of such processes.

BACKGROUND OF THE INVENTION

The covalent site-specific modification of proteins is a crucial process in biological systems. Enzymatic modifications (such as phosphorylation, glycosylation, sulfation, acetylation, methylation, isoprenylation, ubiquitination, sumoylation, neddylation) play a defining role in cellular processes including protein localization and trafficking, signal transduction, transcriptional regulation, and targeted protein destruction. Reproducing natural modifications on the surface of proteins is invaluable for studying their function.

The site-specific covalent addition of 'unnatural' moieties, such as fluorophores, affinity labels, spin-label probes, radio-labels and other (bio-orthogonal) functional groups, to proteins and peptides has also proven useful for a vast variety of applications and processes both in vivo and in vitro.

With the advances in biocompatible synthetic organic chemistry, a whole new field of opportunity has opened up, affording high diversity in the nature of the ligation components as well as a choice of ligation reactions. Chemical ligation involves the chemoselective covalent linkage of a first chemical component to a second chemical component. Unique, mutually reactive functional groups present on the protein or peptide and on the second ligation component can be used to render the ligation reaction chemoselective. Developing robust methods for selectively modifying proteins or peptides is however still quite a challenge, due to the variety and number of functionalities present in a typical protein. There is, in general, a desire or need to modify the protein site-specifically to optimally combine the conjugated functionality with the intrinsic properties of the protein or peptide. For controlled, selective access to such modified proteins, a unique, bio-orthogonal, chemical handle or attachment site is thus often required for ligation or conjugation of a desired molecule thereto.

Most methods to produce bioconjugates exploit the nucleophilicity of either amines (lysine side chains and the N-terminus) or thiols (cysteine side chains) on the protein surface. For site-specific modification of proteins methods have been proposed that include designing mutants having all of the lysine residues of a protein replaced or a mutant having all but one of the cysteine residues replaced, in order to limit the modification site to a single location.

Activated acids such as N-hydroxysuccinimidyl-esters can be used to target amines; however, proteins typically contain multiple amines and, even with the reduced $pK_a$ of the amino-terminus of the protein compared to the lysine side chain, this labelling is generally nonspecific. To overcome this problem, researchers have gone as far as evolving the protein target to eliminate all surface lysines. Researchers performed phage display selections on tumour necrosis factor-α (TNF-α) to evolve a protein without any lysines, allowing for the site-specific PEGylation of the single remaining amine at the N-terminus. The evolved TNF-α with modification at just the N-terminus has improved stability and bioactivity compared to the randomly labelled wild-type TNF-α. In general, large-scale amino acid-substitution that replaces a given type(s) of amino acid at most of all sites has been associated with the drawback of reduced protein activity.

Cysteine labelling is typically more specific than amine labelling as the thiol group is more nucleophilic and a single cysteine can be introduced by site-directed mutagenesis without affecting the function of the protein. Cysteines introduced by mutagenesis are labelled with small molecule-linked maleimides, α-haloketones, or other electrophilic groups that preferentially react with thiols. However, cysteine-based methods alone cannot easily perform multiple modifications to a protein (such as introducing two fluorophores for fluorescence resonance energy transfer (FRET) analysis) except when the reactivity of the two cysteines is quite different, and not all protein targets allow for the introduction of cysteines without impairing function.

Further methodologies that target additional functionalities present in the natural amino acids are considered to be valuable additions to the chemist's toolbox for performing protein modification.

Francis and co-workers (*J. Am. Chem. Soc.* 2004, 126, 10256) have identified reactions that can specifically target both tryptophan and tyrosine residues. Using rhodium carbenoids, the selective modification of the indole functionality in tryptophan (at N-1 or at C-2) can be achieved. When applied to either myoglobin or subtilising Carlsberg (with 2 and 1 surface tryptophans, respectively), modification occurs exclusively at the tryptophan residues in about 50-60% yield. While the system requires a co-solvent to solubilize the organic reagents, this co-solvent (ethylene glycol) is not expected to denature the protein targets. A more significant limitation of the chemistry is the requirement of extremely low (1.5-3.5) pH that causes denaturation of most proteins as well as loss of myoglobin's heme group. While methods to reconstitute myoglobin could recover that protein's structure, these extreme conditions will be incompatible with many targets. The results do suggest, however, that transition metal complexes can be used for specific bioconjugation of aromatic residues in proteins.

Francis and co-workers (*J. Am. Chem. Soc.* 2004, 126, 15942) have also described a Mannich-type reaction to selectively target tyrosines using an aldehyde and an aniline at pH 6.5. By attaching a fluorophore to the aniline, conjugation of rhodamine to chymotrypsinogen A is achieved without altering the protein's activity. The relative surface accessibility of different tyrosines allows for selectivity for particular tyrosine residues; for chymotrypsinogen A, one of the three surface tyrosines is preferentially targeted.

Some strategies make use of functional groups that do not occur naturally. Such amino acids can be introduced by methods including total synthesis, semi-synthesis by ligation of synthetic and biologically expressed fragments, transfer reactions, etc. The presence of these non-naturally occurring functional bio-orthogonal groups enables individual targeting without inadvertent cross-linking or other reactions with naturally occurring amino acid side chain groups.

An example includes the controlled introduction of azides in proteins as the bio-orthogonal ligation handle. A reaction that has proven useful in this regard is the Sharpless modified Huisgen cyclization of an alkyne and an azide. In the presence of catalytic amounts of Cu(I), this cyclization occurs chemoselectively to produce a 1,4-disubstituted triazole ring. Cross reactivity with common biological functional groups is not seen for either the alkyne or the azide, and both groups are stable under biological conditions. This reaction has been used for applications ranging from the modification of viral particles and proteins on cell surfaces to the identification of carbohydrate-binding proteins and cellular proteins tagged by small-molecule activity probes.

As will be clear from the above, despite the extraordinary interest in selectively modified proteins, each of the techniques currently available suffers from specific draw-backs. Over and above that, there is quite a lack of generally usable and flexible methods. Hence, additional chemical strategies for providing selective (bio-orthogonal) ligation handles are still needed to complement and expand upon methods from biology. It is the objective of the present invention, to provide such strategies.

SUMMARY OF THE INVENTION

The present invention provides a new and generally applicable approach to site- and chemoselective modification of peptides and proteins, which is particularly fast, flexible and economical. In accordance with the invention, certain novel lysine compounds are employed as building blocks in protein or peptide synthesis, providing the specific ligation handle(s) for site- and chemoselective modification.

In particular, the invention entails the use of specific thiolysine and selenolysine compounds, notably the compounds 5-thiolysine (also referred to as δ-thiolysine) and 4-thiolysine (also referred to as γ-thiolysine) as well as 5-selenolysine (also referred to as δ-selenolysine) and 4-selenolysine (also referred to as γ-selenolysine), for the site- and chemoselective modification of a peptide or protein. The lysine compounds of the present invention are easily synthesized in high yield from commercially available building blocks, involving, a relatively low number of synthetic steps, as will be illustrated herein.

The design of the present lysine compounds has two important features. First, the positioning of the thiol or selenol group at the respective carbon allows for a very efficient intramolecular transfer reaction to take place. Secondly, the thiol or selenol group can subsequently be removed using reported procedures, thereby restoring the native lysine structure, or be used as an additional conjugation handle. The methodology is fast and gives well-defined material.

The presence of the thiol or selenol residue in the vicinity of the ε-amine or, where applicable, the α-amine of lysine allows for very favourable S to N or Se to N transesterification reactions, whereby a selected functional agent, introduced in the peptide or protein through thio- or selenoesterification, is transferred to said ε-amine or α-amine.

As will be explained in great detail in the examples, the present inventors have demonstrated the application of a lysine building block of the invention in the ubiquitylation of selected peptide targets. By employing an E1-mediated synthesis of full-length ubiquitin thioester and the newly developed amino acid 5-thiolysine, the inventors demonstrated site-specific ubiquitylation of lysine residues in selected target peptides, based on H2B, PCNA, PTEN and p53. This methodology is also readily adaptable to other functional agents or ligands. The use of mild desulfurization conditions after ligation do not affect the functional integrity of other building blocks present in the peptide or protein or the selected functional agent.

In summary, the present invention concerns certain lysine compounds, methods for synthesizing them and their use as building block in protein or peptide synthesis, typically as bio-orthogonal target for site- and chemoselective modifications of polypeptide or protein sequence. The invention also concerns methods of synthesizing and modifying selected protein or peptide sequences using the present lysine compounds. Furthermore, the invention concerns the intermediate and end-products obtained in such methods. These and other aspects of the invention, as defined in the appending claims, will be described and exemplified in more detail in the following description and examples.

DETAILED DESCRIPTION OF THE INVENTION

A first aspect of the invention concerns a lysine compound represented by formula (Ia) or (Ib):

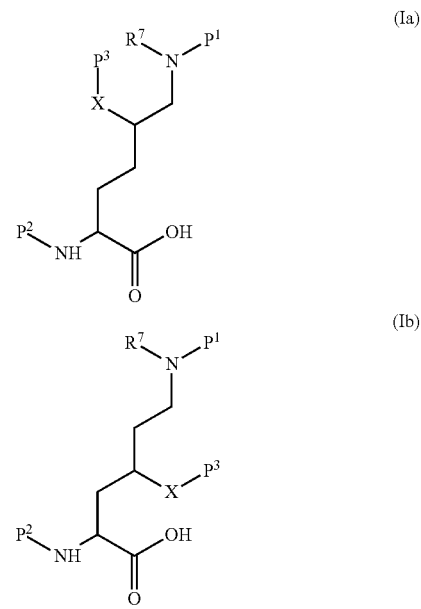

wherein —X— represents (i) sulphur or (ii) selenium; —$P^1$ and —$P^2$ independently represent (i) hydrogen or (ii) an amine protecting group; —$P^3$ represents (i) hydrogen; (ii) an alkylthio, alkenylthio, alkylseleno or alkenylseleno group represented by the formula —X—$R^6$, wherein —$R^6$ represents an optionally substituted branched or straight chain, aliphatic or cyclic alkyl, heteroalkyl, alkenyl or heteroalkenyl moiety; (iii) a thiol or selenol protecting group; or (iv) a moiety —$R^5$ or (v) a moiety represented by the formula —C(=O)—$R^{5'}$; —$R^5$ and —C(=O)—$R^{5'}$ represent a residue of a covalently bound ligand, preferably selected from the group consisting of peptides, lipids, carbohydrates, polymers, organic agents and inorganic agents; and —$R^7$ represents (i) hydrogen or (ii) an optionally substituted branched or straight chain, aliphatic or cyclic alkyl, heteroalkyl, alkenyl or heteroalkenyl moiety; or an ester, salt, solvate or hydrate of said lysine compound.

In the above formulae —X— can represent sulphur or selenium. The thiolysine and selenolysine compounds can be obtained and used in similar ways. Nevertheless, it was found that the benefits of the present invention are most pronounced for the thiolysine compounds. Hence, a particularly preferred embodiment of the invention concerns lysine compounds as defined above wherein —X— represents —S—.

In the above formulae —$P^1$ and —$P^2$ may independently represent hydrogen or an amine protecting group. As will be understood by the skilled person, the present invention provides lysine compounds in unprotected, partly protected or completely protected form. Since the use of the compounds in peptide synthesis will typically require protection of all functional groups, a particularly preferred embodiment of the invention concerns protected lysine compounds according to formula (Ia) or (Ib), wherein —P1 and —P2 represent independently selected amine protecting groups.

The term 'amine protecting group' refers to any organic moiety which is readily attached to an amine nitrogen atom, and which, when bound to the amine nitrogen, renders the resulting protected amine group inert to the reaction conditions to be conducted on other portions of the compound and which, at the appropriate time, can be removed to regenerate the amine group. Examples of such amine protecting groups are known to the person skilled in the art and include, but are not limited to: acyl types such as formyl, trifluoroacetyl, phthalyl, and p-toluenesulfonyl; aromatic carbamate types such as benzyloxycarbonyl (Cbz) and substituted benzyloxy-carbonyls, 1-(p-biphenyl)-1-methylethoxy-carbonyl, and 9-fluorenylmethyloxycarbonyl (Fmoc); aliphatic carbamate types such as tert-butyloxycarbonyl (Boc), ethoxycarbonyl, diisopropylmethoxycarbonyl, and allyloxycarbonyl; cyclic alkyl carbamate types such as cyclopentyloxycarbonyl and adamantyloxycarbonyl; alkyl types such as trityl and benzyl; trialkylsilane such as trimethylsilane; and thiol containing types such as phenylthiocarbonyl and dithiasuccinoyl. Preferably the amine protecting group in accordance with the present invention is selected from the group consisting of Cbz; p-Methoxybenzyl carbonyl; Boc; Fmoc; Benzyl; p-Methoxybenzyl; 3,4-Dimethoxybenzyl; p-methoxyphenyl; Tosyl; sulfonamides; allyloxycarbonyl; trityl and methoxytrityl, all of which are, as such, commercially available and well-known in the art. Due to their wide-spread application, the exact chemistry involved in the use of these groups in peptide synthesis has been described extensively and is part of the skilled person's common general knowledge. Amine protecting groups and protected amine groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

In the above formulae —$P^3$ may represent an alkylthio, alkenylthio, alkylseleno or alkenylseleno group represented by the formula —X—$R^6$, —$R^6$ representing an optionally substituted branched or straight chain, aliphatic or cyclic alkyl, heteroalkyl, alkenyl or heteroalkenyl moiety. As used herein the term 'optionally substituted' is meant to encompass any kind of alkyl, heteroalkyl, alkenyl or heteroalkenyl which may comprise one or more substituents. Said substituents may typically incorporate one or more heteroatoms, such as nitrogen, oxygen, sulfur, phosphorus, boron, chlorine, bromine, or iodine. When —$P^3$ represents a moiety of formula —X—$R^6$, typically, disulphide or diselenide compounds are provided, as will be understood by the skilled person, in which form the functional group at the γ- or δ-position can effectively be blocked or protected. Hence, since the minimal function of the —X—$R^6$ moiety, if present, is only to block the thiol or selenol moiety, e.g. during protein or peptide synthesis, the exact structure of —$R^6$ is not crucial. In a preferred embodiment —$R^6$ represent an optionally substituted lower alkyl or alkenyl moiety, more preferably an optionally substituted $C_1$-$C_4$ alkyl or an optionally substituted $C_2$-$C_4$ alkenyl, most preferably a methylsulfide.

Furthermore, —$P^3$ in the above formulae may represent a thiol or selenol protecting group. The terms 'thiol protecting group' and 'selenol protecting group' refer to any organic moiety which is readily attached to a thiol sulphur atom or a selenium atom, and which, when bound to said atom, renders the resulting protected group inert to the reaction conditions to be conducted on other portions of the compound and which, at the appropriate time, can be removed to regenerate the thiol or selenol group. Suitable examples of such protecting groups are known to the person skilled in the art. Preferably the protecting group in accordance with the present invention is selected from the group consisting of benzyl; 4-methoxybenzyl; trityl; methoxytrityl; t-butyl; t-butylthiol; methylthiol; acetyl; 3-nitro-2-pyridinesulphenyl; acetamidomethyl; Cbz and 2-nitrobenzyl. The use of thiol-protecting groups is well known in the art, cf, for example, T. H. Greene and P. G. M. Wuts, Protective Groups in Organic Synthesis, 3rd edition, John Wiley & Sons, New York (1999).

In the above formulas, —$R^5$ and —C(=O)—$R^{5'}$ represent a residue of a covalently bound ligand. Said ligand is preferably selected from the group consisting of peptides, lipids, carbohydrates, polymers, organic agents and inorganic agents. In a preferred embodiment said ligand comprises a carboxyl group through which it is attached to the sulphur or selenium atom, in which case —$P^3$ represents an acyl. It is to be understood that —$R^5$ is used herein to denote a ligand without any restrictions as to the nature of the bond between the ligand and the present lysine building block. Hence, the formula —C(=O)—$R^{5'}$, which is used to refer specifically to a thio- or seleno-ester of a ligand containing a carboxyl group, is encompassed by —$R^5$. As will be explained in more detail hereafter, an acyl, i.e. a moiety represented by the formula —C(=O)—$R^{5'}$, can be transferred to the ε-amine (or, in certain cases, the α-amine) of the lysine building block. If the residue of the ligand, —$R^5$, is not an acyl, such an intramolecular transfer is typically not possible, because the bond is less reactive. As a further consequence of said bond being less reactive, peptides can conveniently be synthesized using a lysine building block of the invention wherein —$R^5$, where it does not represent an acyl, is already present. If, in the peptide, a ligand is to be incorporated as a thio- or seleno-ester, i.e. where said residue of the ligand is an acyl, it is more convenient to perform ligation after synthesis of the peptide.

Hence, in a preferred embodiment of the invention —$R^5$ in formula (Ia) or (Ib) does not represent an acyl moiety, i.e. it represents a moiety other than —C(=O)—$R^{5'}$, preferably it represents a primary, secondary or tertiary carbon structure, such as an optionally substituted primary, secondary or tertiary aliphatic or cyclic alkyl, heteroalkyl, alkenyl or heteroalkenyl, yielding a thio- or seleno-ether compound. In a particularly preferred embodiment —$R^5$ in formula (Ia) or (Ib) represents a carbohydrate such as galactose.

Within the context of the present invention, the meaning of the term 'ligand' as such will be clear to the person skilled in the art. In particular, since the present invention aims at providing a new method of site- and chemoselective modification of proteins or peptides it will be clear that said term is meant to include e.g. any agent the conjugation of which to a selected peptide or protein has been described or suggested in the art for a certain purpose. The introduction of the ligand typically introduces or affects a particular functionality of said peptide or protein (which may therefore also be referred to herein as 'functional agent' or the like). Particularly preferred examples of such ligands or functional agents include dyes, probes, labels, tags, solubility-modifying agents, enzyme targets, receptor ligands, immunomodulatory agents, co-factors, and cross-linking agents. In an embodiment the ligand is a therapeutic agent. In the examples hereafter ligation of certain peptides with ubiquitin and ubiquitin-like proteins is disclosed. In the above formula, —$R^7$ may represent an optionally substituted branched or straight chain, aliphatic or cyclic alkyl, heteroalkyl, alkenyl or heteroalkenyl moiety. The presence of such a group will, after intramolecular transfer of the —C(=O)—$R^{5'}$ moiety, yield a tertiary ε-amide, which typically can not be hydrolysed by proteases. This provides a particular advantage, e.g. when the lysine building block is incorporated for ubiquitination of a peptide or protein. In a particularly preferred embodiment of the invention, —$R^7$ in the above formula (Ia) and (Ib) represents (i) hydrogen or (ii) an optionally substituted branched or straight chain alkyl, such as a lower alkyl, such as methyl or ethyl.

As will immediately be recognized by the skilled person, the lysine compounds of the invention contain 2 centres of chirality, such that four potential stereoisomers are possible. The present invention encompasses (the use of) any isomerically pure compound as well as any racemic or non-racemic mixture. Given the intended application of the present lysine compounds, the natural L-amino acid configuration is particularly preferred. Thus, an embodiment of the invention concerns a lysine compound as defined herein above wherein the α-carbon atom has the L-configuration.

Esters, salts, hydrates, solvates and other derivatives of these thiolysine compounds are also within the ambit of the invention. Any such derivative may thus be provided without departing from the scope of the invention, provided it is still suitable for use as a building block in protein or peptide synthesis to provide the bio-orthogonal ligation handle, without the need for major chemical modification prior to said use.

In a particularly preferred embodiment of the invention a lysine compound according to formula (Ia) is provided wherein —X— represents sulphur; —$P^1$ represents an amine protecting group selected from Fmoc, Boc, trityl or methoxytrityl; —$P^2$ represents an amine protecting group selected from Fmoc, Boc, trityl or methoxytrityl; —$P^3$ represents —S—$CH_3$, trityl or methoxytrityl; and $R^7$ represents, hydrogen or methyl; or salts, esters, hydrates or solvates thereof.

In another particularly preferred embodiment of the invention a lysine compound according to formula (Ib) is provided wherein —X— represents sulphur; —$P^1$ represents an amine protecting group selected from Fmoc, Boc, trityl or methoxytrityl; —$P^2$ represents an amine protecting group selected from Fmoc, Boc, trityl or methoxytrityl; —$P^3$ represents —S—$CH_3$, trityl or methoxytrityl; and $R^7$ represents, hydrogen or methyl; or salts, esters, hydrates or solvates thereof.

A second aspect of the invention concerns the synthesis of the lysine compounds as defined herein before, said method comprising the steps of (i) treating a 4-hydroxylysine or 5-hydroxylysine, represented by formula (IIIa) or (IIIb), with an organoborane compound to obtain an amino acid protected compound, which is subsequently reacted with an amine protecting group, yielding the protected 4-hydroxylysine or 5-hydroxylysine, represented by formula (IVa) or (IVb); (ii) mesylating the compound obtained in step (i) and subsequently reacting it with a suitable thiocarboxylic acid or selenocarboxylic acid or salt or ester thereof to yield the corresponding thio- or seleno-ester, as represented by formula (Va or Vb); (iii) hydrolysis of the thio- or selenoester obtained in step (ii) with an aqueous solution of an alkali metal hydroxide, yielding the thiol or selenol compound, which is subsequently reacted with an agent that is able to transfer a group —$P^3$ as defined herein before, to said thiol or selenol group, yielding a compound represented by formula (VIa) or (VIb); and (iv) removing the amino acid protecting organoborane group, and, optionally, subsequently reacting the compound with an amine protecting agent, to yield the compound according to formula (Ia) or (Ib) as defined here above. In the formulae (IIIa-VIa) and (IIIb-VIb), —X—, and —$P^3$ have the same meaning as defined here above in relation to formulae (Ia) and (Ib). In said formulae, —$P^1$ represents an amine protecting group as defined above.

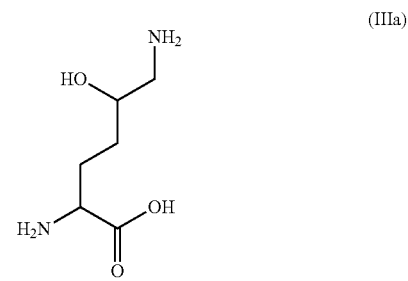

(IIIa)

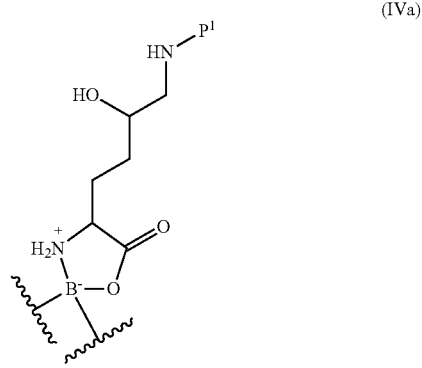

(IVa)

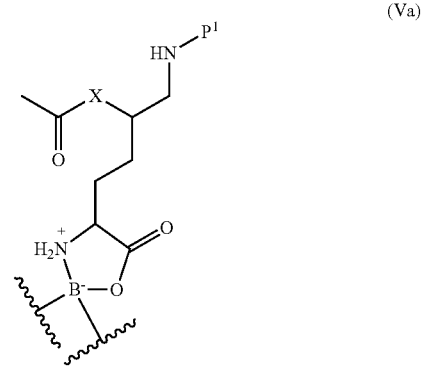

(Va)

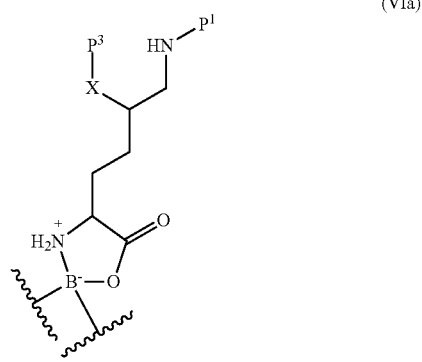

(VIa)

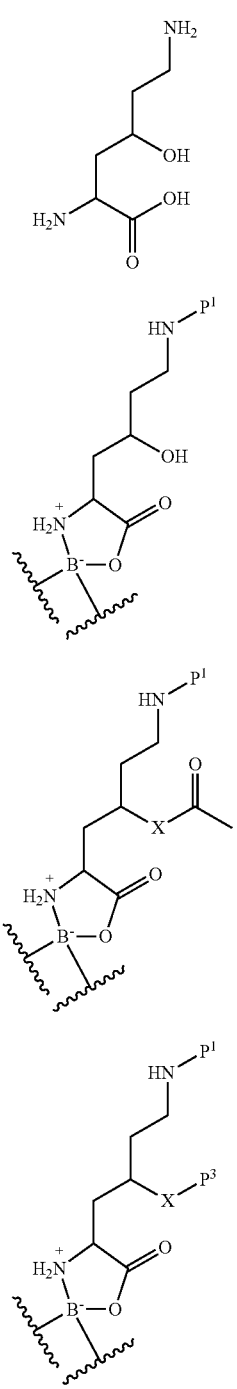

Compound (IIIb), 4-Hydroxylysine, can be obtained by synthesis (J. Marin, C. Didierjean, A. Aubry, J. R. Casimir, J. P. Briand, G. Guichard J. Org. Chem. 2004, 69, 130). Compound (IIIa), 5-Hydroxylysine, is commercially available, for example from Bachem or Sigma Aldrich. 5-Hydroxylysine is available in enantiomeric pure form (i.e. the natural 2S/5R form) and as a mixture of the four possible isomers (5S/R and D/L). All forms can be used in the synthesis of the corresponding protected lysine building blocks.

As stated above, the synthesis preferably starts with the simultaneous protection of the α-amino acid group by treatment with an organoborane compound. A particularly preferred example of such an organoborane compound is 9-borabicycloborane (9-BBN), the use of which for protecting functionalized amino acids has been described in the art. Typically such a reaction is performed by adding solid crystalline hydroxylysine to a solution of 9-BBN or other organoborane in a suitable solvent, e.g. hot methanol, and subsequently refluxing under an inert atmosphere. After completion of the reaction, the solvent is typically evaporated and the residue is dissolved in a suitable solvent and reacted with the amine protecting agent, e.g. di-tert-butyl dicarbonate. The compound according to formula (IVa) or (IVb) can subsequently be isolated and purified by any suitable method known by the skilled person, e.g. using extraction and silica gel purification.

Subsequently, the compound of formula (IVa) or (IVb) is converted to the corresponding thio- or selenoester of formula (Va) or (Vb) by mesylation and subsequent reaction with a suitable thiocarboxylic acid or selenocarboxylic acid or salt or ester thereof. Typically the compound of formula (IVa) or (IVb) is first mesylated by reacting it, in a suitable solvent, with a mesylate such as MsCl. The mesylated compound may be isolated and purified in using common techniques known by the skilled person. The mesylated compound is then reacted with said thioacetic or selenoacetic acid or salt thereof in a suitable solvent to yield the corresponding thio- or seleno-ester. In a preferred embodiment of the invention thioacetic or selenoacetic acid or a salt thereof is used. After the reaction is substantially completed common isolation and/or purification techniques may be employed to yield the reaction product as a highly pure solid.

Next, hydrolysis of the thio- or selenoester with an aqueous solution of an alkali metal hydroxide, such as NaOH, furnishes the thiol or selenol which, can be converted to any other compound of formula (VIa) or (VIb) by combining it, in a suitable solvent, with an agent that can transfer a group —$P^3$ to said thiol or selenol, to yield the compound of formula (VIa) or (VIb). For example, a thioester represented by formula (Va) may be converted to the corresponding thiol using 1N NaOH, which thiol, in solution, is subsequently combined, drop-wise, with a solution of S-methyl methanethiosulfonate yielding the compound of formula (VIa) wherein —X—$P^3$ represents —S—S—$CH_3$.

Finally, removal of the amino acid protecting organoborane moiety of the compound of formula (VIa) or (VIb), typically by heating the compound in a suitable solvent, e.g. to 70° C. in a solution of ethylene diamine in THF, and subsequent treatment of the compound with a suitable amine protecting group, yields the protected compound of formula (Ia) or (Ib). As will be understood by the skilled person the corresponding unprotected compounds can be obtained by omitting the last step of reacting with an amine protecting group, and, if desired, by removing any other protecting groups.

In an alternative embodiment of the invention the above-described method can start from corresponding chloro- or bromolysines instead of hydroxylysines, with the particular advantage that the additional step of mesylation of the intermediate can be omitted. In accordance with this embodiment of the method, step (i) comprises treating a 4-chlorolysine, 5-chlorolysine, 4-bromolysine or 5-bromolysine compound with an organoborane compound to obtain an amino acid protected compound, which is subsequently reacted with an amine protecting group, yielding the protected 4-chlorolysine, 5-chlorolysine, 4-bromolysine or 5-bromolysine; step (ii) comprises reacting the compound obtained in step (i) with a suitable thiocarboxylic acid or selenocarboxylic acid or salt thereof to yield the corresponding thio- or seleno-ester; and steps (iii) and (iv) are as described herein above.

Since all of the above reactions are per se known in the art, albeit in relation to the synthesis of different compounds, it is entirely within the skills of the trained professional to determine proper and optimal reaction conditions for each of the above steps as well as to apply any additional isolation or purification technique between the above steps in order to obtain the desired compound in the highest possible yield. A complete step by step description of the synthesis of certain compounds of the invention is given in the examples below.

The present invention also concerns any of the intermediate products obtained in the synthesis of the present lysine compounds, in particular those represented by the above formulae (IIIa-VIa) and (IIIb-VIb).

A third aspect of the invention concerns a peptide represented by formula (IIa), (IIb) or (IIc):

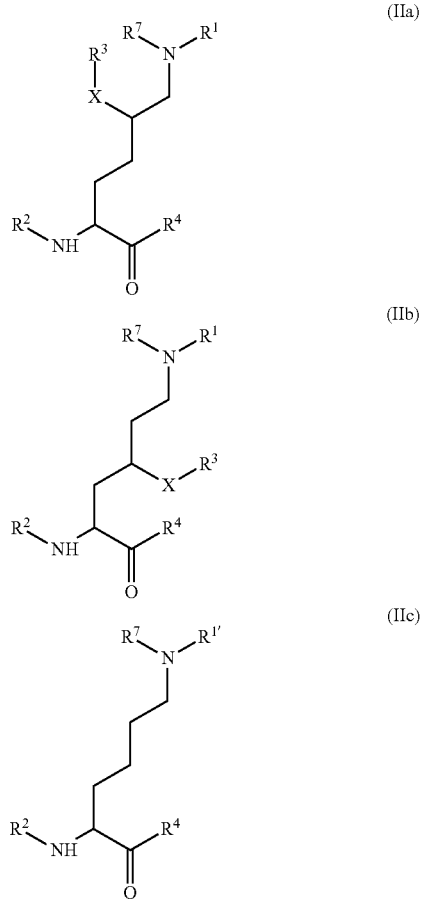

wherein
—R¹ represents (i) hydrogen; (ii) —P¹ as defined here above in relation to formulae (Ia) and (Ib); or (iii) a moiety represented by the formula —C(=O)—R⁵'; —R¹' represents a moiety represented by the formula —C(=O)—R⁵'; —R² represents (i) hydrogen; (ii) —P² as defined here above in relation to formulae (Ia) and (Ib); (iii) a C→N polypeptide chain or (iv) a moiety represented by the formula —C(=O)—R⁵'; —R³ represents (i) hydrogen; (ii) —P³ as defined here above in relation to formulae (Ia) and (Ib); (iii) a moiety —R⁵; or (iv) a moiety represented by the formula —C(=O)—R⁵'; —R⁴ represents (i) —OH or (ii) an N→C polypeptide chain; —X— represents (i) sulphur or (ii) selenium; —R⁵ and —C(=O)—R⁵' have the same meaning as defined here above in relation to formulae (Ia) and (Ib); and —R⁷ represents (i) hydrogen or (ii) an optionally substituted branched or straight chain, aliphatic or cyclic alkyl, heteroalkyl, alkenyl or heteroalkenyl moiety; with the proviso that in the respective formula at least one of —R² and —R⁴ represents a polypeptide chain.

The peptides of the present invention preferably are non-naturally occurring peptides, where the term non-naturally occurring is used to indicate that peptides occurring in nature are not comprised within the scope of the invention, regardless of whether they were actually obtained by a process of the invention. Peptides differing from a naturally occurring peptide by the presence of the lysine building block of the invention and/or the presence of the group —R⁵ or —C(=O)—R⁵', are understood herein to constitute non-naturally occurring peptides and are thus encompassed by the scope of the claims.

As will be clear to the skilled person, the above peptides according to formulae (IIa), (IIb) and (IIc), depending on the specific meanings of —R¹, —R², —R³ and —R⁴, constitute the intermediate and end-products of the processes of the invention, i.e. of peptide or protein synthesis wherein one or more of the above thio- or selenolysine building blocks are incorporated, and subsequent site- and chemoselective modification by covalent attachment of a ligand. The details of the relevant reaction pathways are given here below.

As will be evident to the skilled person, the N→C backbone of the peptide of the invention is represented by the R²→R⁴ chain. The ligand or functional agent which is covalently bound to the peptide using the ligation handle of the invention may also be a peptide, such that in some embodiments, a second peptide chain may be present orthogonally attached to the primary backbone represented by the R²→R⁴ chain. As will be explained in more detail hereafter, if a lysine building block of the invention according to formula (Ib) is incorporated as the N-terminal amino acid of the R²→R⁴ chain, i.e. when R² in formula (IIb) represents hydrogen instead of a peptide chain, the ligation handle may facilitate attachment of the modification ligand at the α-amine group instead of the ε-amine group. If in that case the ligand is also a peptide, the resulting 'modified' peptide may, depending on any further modification steps, comprise a single peptide chain. Such ligation products are also within the scope of the invention, provided they are not identical to a naturally occurring peptide or protein, as explained before.

The present invention, as noted before, provides the possibility of including in a peptide or protein sequence of interest, a ligation handle for site- and chemoselective modification. In accordance with one embodiment of the present invention, it is particularly preferred that the ligation handle is located within the peptide or protein sequence of interest instead of at the C- or N-terminus of said sequence. Hence, a preferred embodiment of the invention provides a non-naturally occurring peptide as defined herein before wherein, R² and R⁴ both represent a polypeptide chain. In accordance with another preferred embodiment however, it is preferred that the present thio- or seleolysine ligation handle is located at the N-terminus of the peptide, for reasons explained in more detail hereafter. Hence, another preferred embodiment of the invention provides a non-naturally occurring peptide as defined herein before, preferably according to formula (IIb), wherein, —R⁴ represents a polypeptide chain and —R² represents —P² or hydrogen.

As will be understood by the skilled person, said ligation handle can be incorporated in the peptide or protein of interest either by addition of the lysine building block of the invention to said sequence or by substitution of an amino acid residue from said sequence by the residue of a lysine building block of the invention, in particular by the substitution of a 'natural' lysine residue.

Hence in one preferred embodiment, a non-naturally occurring peptide as defined herein before is provided, wherein —$R^2$ and —$R^4$ are chosen such that they include complementary parts of a full amino acid sequence of a naturally occurring polypeptide or protein or functional variant or fragment thereof. In the context of this invention, the term 'complementary parts' (or 'complementary fragments') is used to indicate that the respective parts (or fragments), in a given direction, can be fitted together in a consecutive order to form or include the respective amino acid sequence, typically without gaps or regions of overlap between said parts or fragments.

In another equally preferred embodiment, a non-naturally occurring peptide as defined herein before is provided, wherein, —$R^2$ and —$R^4$ are chosen such that they represent the C→N and N→C polypeptide parts flanking a selected single amino acid residue, preferably a lysine residue, in an amino acid sequence of a naturally occurring polypeptide or protein or functional variant or fragment thereof.

The specific choice of said naturally occurring polypeptide or protein is not critical for the purpose of the present invention as will be recognized by the skilled person. Any polypeptide or protein, the modification of which may be of interest to the skilled person, e.g. for studying and/or modifying its natural course of action in vivo or in vitro, may be employed, without departing from the scope of the invention. In the examples hereafter modification of p53, PTEN, histone H2B and PCNA in accordance with the invention is disclosed.

A functional variant of the naturally occurring polypeptide or protein, may differ from said naturally occurring polypeptide or protein by minor modifications, such as substitutions, insertions, deletions, additional N- or C-terminal amino acids, and/or additional chemical moieties, but maintains the basic polypeptide and side chain structure of the naturally occurring form as well as the ability to elicit a certain biological function or activity in vitro and/or in vivo. Typically, when optimally aligned, such as by the programs GAP or BESTFIT using default parameters, a naturally occurring polypeptide and a homologue thereof share at least a certain percentage of sequence identity. GAP uses the Needleman and Wunsch global alignment algorithm to align two sequences over their entire length, maximizing the number of matches and minimizes the number of gaps. Generally, the GAP default parameters are used, with a gap creation penalty=8 and gap extension penalty=2. For proteins the default scoring matrix is Blosum62 (Henikoff & Henikoff *PNAS*, 1992, 89, 915). Sequence alignments and scores for percentage sequence identity may be determined using computer programs, such as the GCG Wisconsin Package, Version 10.3, available from Accelrys Inc., 9685 Scranton Road, San Diego, Calif. 92121-3752, USA. Alternatively percent similarity or identity may be determined by searching against databases such as FASTA, BLAST, etc. A 'functional variant thereof' herein is understood to comprise a polypeptide or protein having at least 70%, preferably at least 80%, more preferably at least 90%, still more preferably at least 95%, still more preferably at least 98% and most preferably at least 99% amino acid sequence identity with the selected naturally occurring polypeptide of interest mentioned above and is still capable, under the proper conditions, of eliciting its normal functions to a significant extent.

As will be understood by the skilled person modifications that may in particular be employed in accordance with the invention, comprise inclusion of further ligation handles, such as those in accordance with the present invention. In a particularly preferred embodiment, one or both of the peptide chains —$R^2$ and —$R^4$ comprises one or more additional lysine building blocks of the invention. Even more preferably, a peptide as defined before is provided, comprising two or more lysine building blocks of the invention, providing ligation handles with differential reactivity. For example, a peptide may be provided comprising a first lysine building block of the invention wherein —X— represents sulphur and a second lysine building block of the invention wherein —X— represents selenium. In another embodiment, a peptide may be provided comprising a first lysine building block of the invention and a second lysine building block, wherein —X— may be the same or different, and wherein the groups —$P^3$ in both building blocks are different. Further embodiments are provided wherein more than two building blocks are included each having differential reactivity, by suitable selection of —X— and —$P^3$. As will be understood, by the skilled person, in accordance with such embodiments the inclusion of two or more identical building blocks may also be envisaged.

The term 'a functional fragment thereof' refers to a peptide fragment that is a portion of a full length naturally occurring polypeptide or protein or functional variant thereof, provided that the portion has the ability to elicit a biological function or activity, that is characteristic of the corresponding full length sequence.

In the above formulas (IIa-IIc), —$R^5$ and —C(=O)—$R^{5'}$ represent the residue of a covalently bound ligand, as defined and explained here above in relation to formulae (Ia) and (Ib).

In an embodiment of the invention a preferred ligand is ubiquitin or an ubiquitin-like protein. Ubiquitin conjugation or ubiquitylation is a process, occurring naturally in all eukaryotes, that has been implicated in a wide variety of critical cellular processes including protein stability, cell cycle progression, transcriptional control, receptor transport and the immune response. Ubiquitin and ubiquitin-like proteins are ~100 aa polypeptides. To date, approximately 12 different ubiquitin-like proteins have been identified, including NEDD8, ISG15, FUB1, FAT10, UBL5, SUMO-1, SUMO-2, SUMO-3, UFM1, MLP3A-LC3, ATG12 and URM1. Peptides as described above, wherein said ligand is ubiquitin or one of said ubiquitin-like proteins are particularly preferred. In the examples hereafter ligation of certain peptides with ubiquitin and ubiquitin-like proteins is disclosed. For more detailed information regarding the function and structure of ubiquitin and ubiquitin-like proteins Jeram and co-workers (*Proteomics* 2009, 922-934) may be referred to, the contents of which are incorporated herein by reference.

In a particularly preferred embodiment of the invention, a peptide is provided according to formula (IIa), wherein —$R^2$ and —$R^4$ both represent a polypeptide chain; at least one of —$R^1$ and —$R^3$ represents the residue of a covalently bound ligand as defined above; —$R^7$ represents hydrogen or methyl and —X— represents sulphur.

In another particularly preferred embodiment of the invention, a peptide is provided according to formula (IIb), wherein —$R^2$ and —$R^4$ both represent a polypeptide chain; at least one of —$R^1$ and —$R^3$ represents the residue of a covalently bound ligand as defined above; —$R^7$ represents hydrogen or methyl and —X— represents sulphur.

In another particularly preferred embodiment of the invention, a peptide is provided according to formula (IIc), wherein —$R^2$ and —$R^4$ both represent a polypeptide chain, preferably chosen such that they include complementary parts of a full amino acid sequence of a naturally occurring polypeptide or protein or functional variant or fragment thereof; —$R^7$ represents hydrogen or lower alkyl, preferably methyl; and —$R^{1'}$ represents the residue of covalently bound ubiquitin or ubiquitin-like protein.

A fourth aspect of the invention concerns a method of site and chemoselective modification of a selected polypeptide or protein sequence comprising i) chemical, biochemical or biological synthesis or production of said selected polypeptide or protein sequence wherein at least one lysine compound according to formula (Ia) or (Ib) is incorporated, by addition or substitution, in said selected sequence, wherein —$P^3$ represents hydrogen or, preferably, a protecting group as defined herein before; ii) removing in the residue of said lysine compound the group represented by —$P^3$ and conjugating a group represented by the formula —$R^5$ or —C(=O)—$R^{5'}$, wherein —$R^5$ and —C(=O)—$R^{5'}$ have the same meaning as defined in relation to formulae (IIa-IIc), with the residue of said lysine compound at the sulphur or selenium atom.

As explained before, a particular advantage of the building blocks of the invention, resides in the possibility of transferring an acyl moiety, —C(=O)—$R^{5'}$, from the thiol or selenol ligation handle to the ε- or, in some case, the α-amine. Hence, in a preferred embodiment of the invention, a method of site- and chemoselective modification is provided as defined herein before, wherein a moiety —C(=O)—$R^{5'}$ is conjugated to the residue of the lysine compound, replacing the group —$P^3$, to yield the corresponding thio- or selenoester and the method comprises the subsequent step iii) of intramolecular transfer of said group represented by formula —C(=O)—$R^{5'}$ to the α- or -ε amine group.

Chemical peptide synthesis methods are well known to the person skilled in the art. In accordance with the present invention the peptides are typically chemically synthesized, preferably using solid phase synthesis. In accordance with the present invention, it is not critical whether the entire sequence is synthesised through stepwise elongation only or whether the process involves ligation of two or more separately obtained fragments. Typically, if the sequence length exceeds 100 amino acids, it may be preferable to produce separate fragments and ligate them through processes known as fragment condensation and/or chemical ligation. As will be explained in more detail hereafter, the present invention also provides a particularly advantageous chemical ligation process for the purpose of peptide synthesis. Alternatively the thio- and selenolysine compounds presented here can be incorporated into a protein using orthogonal tRNA/aminoacyl-tRNA synthetase pairs, which incorporates the unnatural thiolysine building block in response to a nonsense or four-base codon in the gene of the protein of interest. To date this technology has allowed the incorporation of approximately 50 unnatural amino acids (cf. J. M. Xie, P. G. Schultz, Nat. Rev. Mol. Cell. Biol. 2006, 7, 775 and/or P. R. Chen, D. Groff, J. Guo, W. Ou, S. Cellitti, B. H. Geierstanger, and P. G. Schultz, Angew. Chem. Int. Ed. 2009, 48, 4052). For this purpose, the lysine building block of the invention is preferably provided in non-conjugated and, preferably, non-protected form at the α-amine and carboxylic acid.

If the group —$R^5$ represents the afore-mentioned optionally substituted primary, secondary or tertiary aliphatic or cyclic alkyl, heteroalkyl, alkenyl or heteroalkenyl, the conjugation typically comprises a reaction known as Williamson ether synthesis, where the unprotected thiol is reacted with a corresponding compound L-$R^5$, wherein L represents a halogen atom or another good leaving group.

The group represented by the formula —C(=O)—$R^{5'}$ is typically conjugated to the unprotected thiol or selenol group by reacting it with a corresponding acid or ester, typically the carboxylic acid represented by the formula H—O—C(=O)—$R^{5'}$; the thiocarboxylic acid, represented by the formula H—S—C(=O)—$R^{5'}$; or the selenocarboxylic acid, represented by the formula H—Se—C(=O)—$R^{5'}$; or the esters or salts of said acids.

Alternatively, depending on the exact nature of the selected ligand that is to yield the moiety —R5 or —C(=O)—R5' in accordance with the invention, the present method may involve enzymatic conjugation instead of chemical conjugation. In some cases this may be favoured due to, for example, increased specificity and/or mild reaction conditions. Suitable materials and conditions for a given enzymatic conjugation process depend on the exact ligand and will, in general, be known in the art per se.

Intramolecular transfer of the group represented by formula —C(=O)—$R^{5'}$ to the ε-amine group requires deprotection of said amine group, by a reaction known per se in the art, as explained before. The intramolecular S to N transfer of the ligand, also involves standard chemistry. Typically, after deprotection of the amine, the intramolecular S to N transfer is chemically favoured and hence occurs spontaneously, preferably in a neutral or (slightly) alkaline environment. If the lysine building block according to formula (Ib) was used as the N-terminal amino acid residue, the transfer reaction can be directed to the α- or ε-amine group through the specific protection/deprotection steps of the specific amines. It is within the capacities of the skilled person to select the proper protecting groups and reaction conditions for this purpose.

After transfer of the group represented by the formula —C(=O)—$R^{5'}$ to the amine of the lysine building block, an unblocked thiol or selenol group is again available in the residue of the lysine compound of the invention. This group may be used again as a ligation handle to attach a further group represented by —$R^5$ or —C(=O)—$R^{5'}$, which may be the same as or different from the first one, to yield the corresponding conjugate. In case the lysine building block according to formula (Ib) was used as the N-terminal amino acid residue and the second ligand is also an acyl represented by —C(=O)—$R^{5'}$, a second intramolecular transfer may also be available, if desired, as well as the subsequent formation of a conjugate with a third moiety represented by —$R^5$ or —C(=O)—$R^{5'}$, which may be the same or different from the other ones. Alternatively, the thiol or selenol group may be removed from the lysine building block by reactants and conditions known by the skilled person.

As noted before, the synthesis of the peptide is preferably performed on a solid phase substrate, yielding a peptide that is covalently attached to said substrate. One or more of the subsequent steps of the present method may be performed before or after release of the peptide from said solid phase substrate. In an embodiment of the invention conjugation of the ligand to the lysine building block is performed on the solid phase as well. More preferably, the peptide is released from the solid phase substrate after the final modification step of the invention, which may be conjugation, intramolecular transfer or removal of the thiol or selenol group(s). This strategy allows for the modified protein to be obtained directly in high purity, potentially rendering any or all further purification steps superfluous. Alternatively, the method of the invention may concern solid phase synthesis without release from the solid phase substrate prior to or after the subsequent steps of the invention, e.g. in the case of protein (micro) arrays, where the protein can be synthesized directly on the microarray surface.

Although the exact nature of the selected polypeptide or protein sequence is not in any way critical for the purpose of the present invention, a preferred embodiment of the invention concerns a method as defined above, wherein said selected polypeptide or protein sequence is a naturally occurring polypeptide or protein or functional variant or fragment thereof as defined herein above.

Furthermore, in a preferred embodiment said method of site- and chemoselective modification is or includes ubiquitination. Hence, in a preferred embodiment of the invention a method as defined above is provided wherein a moiety —C(=O)—$R^{5'}$ is conjugated to the residue of the lysine compound replacing the group —$P^3$ and said moiety —C(=O)—$R^{5'}$ is ubiquitin or an ubiquitin-like protein.

A fifth aspect of the invention concerns the use of the lysine compounds as defined herein before as building blocks in the synthesis of a selected peptide or protein to provide a ligation handle for the site- and chemoselective modification of said selected polypeptide or protein sequence. As stated before, an embodiment of the invention concerns covalent attachment, typically orthogonal covalent attachment, of a functional ligand, which may be a peptide, to a functional peptide or protein, typically a naturally occurring polypeptide or protein or functional variant or fragment thereof as defined herein above.

Another aspect of the invention, however, concerns the use of the present lysine building block of formula (Ib) for linear attachment of one peptide fragment to another peptide fragment, wherein the C-terminal carboxylic acid group of one fragment is attached to the α-amine group of the other fragments N-terminal thio- or selenolysine building block, as already stated before. This has been found to be a particularly useful tool in synthesis of peptides exceeding a certain length, where it is often desired to attach separately build polypeptide chains to obtain, eventually, a functional peptide or protein, which may or may not contain (bio-orthogonal) functional ligands.

Hence, a further aspect of the invention concerns a method of synthesizing a selected polypeptide or protein sequence comprising i) synthesis of a fragment of said selected polypeptide or protein sequence wherein, as the N-terminal amino acid residue, a lysine compound according to formula (Ib) wherein —$P^3$ represents an amine protecting group as defined herein before, is incorporated by addition or substitution; ii) replacing in said fragment the group represented by —$P^3$ with a complementary peptide fragment of said selected polypeptide or protein sequence, which is attached through the C-terminal carboxyl group; and iii) intramolecular transfer of said complementary peptide fragment to the N-terminal α-amine.

As stated before, in accordance with such a method, after the intramolecular transfer, the thiol or selenol group is again available in the thio- or selenolysine residue as a ligation handle for site- and chemoselective (orthogonal) ligation of a functional agent in accordance with the above described methods and uses. As will be understood by the skilled person such an approach allows a single lysine block to be used very efficiently in the synthesis and subsequent modification of peptides and proteins, and therefore constitutes a particularly preferred embodiment. Alternatively, the thiol or selenol group may be removed after linear ligation of the peptide fragments, if desired.

A further aspect of the present invention concerns the use of the lysine compounds as defined herein before as building blocks in the synthesis of a selected peptide or protein to provide the ligation handle for linear, covalent attachment of individual peptide fragments, in accordance with what has been stated before.

Yet, a further aspect of the invention concerns the use of the peptides or proteins of formulae (IIa-IIc) as defined herein before as a therapeutic or diagnostic agent. As stated before, chemo- and site-selectively modified peptides may find applications in diagnostic and therapeutic methods. For example, endogenous proteins and/or peptides labelled with certain tags, probes or markers may provide useful tools as diagnostic agents. Furthermore, proteins currently known as (potential) therapeutic or diagnostic agents may be modified in accordance with the invention, such as to improve their clinical performance, e.g. by including solubility modifying ligands. Peptidic as well as non-peptidic therapeutic or diagnostic agents may be ligated to a specific protein as the ligand, using the technique of the present invention for targeting of said agent to a specific site of action.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The different aspects of the invention as described here above will be illustrated in the following examples 1-3, and the FIGS. 1-12 referred to therein.

DESCRIPTION OF THE FIGURES

FIG. 1: BenchMark™ Pre-Stained Protein Ladder (Invitrogen)

FIG. 2: SDS-Page (12%) analysis of reaction progression. Reagents and condition: 50 mM Tris-HCl buffer pH 7.5+4 mM $MgCl_2$+2 mM ATP+50 mM MESNa+~178 nM E1+25 µM Ub+2 mM TKAVTK*YTSSK, incubation at 37° C.

FIG. 3: SDS-Page (12%) analysis of minimal required peptide concentration (in µM). Reagents and condition: 50 mM Tris.HCl buffer pH 7.5+4 mM $MgCl_2$+2 mM ATP+50 mM MESNa+~71 nM E1+25 µM Ub, overnight incubation at 37° C.

FIG. 4: SDS-Page (12%) analysis of minimal required E1 concentration (in nM). Reagents and condition: 50 mM Tris-HCl buffer pH 7.5+4 mM $MgCl_2$+2 mM ATP+50 mM MESNa+250 µM TKAVTK*YTSSK+25 µM Ub, overnight incubation at 37° C.

```
1)    p53: HLK*SKKGQSTSRHKKLMFKTEG (2.64 kDa);

2)    p53: HLKSK*KGQSTSRHKKLMFKTEG (2.64 kDa);

3)    p53: HLKSKK*GQSTSRHKKLMFKTEG (2.64 kDa);

4)    p53: HLKSKKGQSTSRHK*KLMFKTEG (2.64 kDa);

5)    p53: HLKSKKGQSTSRHKK*LMFKTEG (2.64 kDa);

6)    p53: HLKSKKGQSTSRHKKLMFK*TEG (2.64 kDa);

7)    PCNA: GDAVVISC*AK*DGVKFSASGELGNGNIKLSQ184
      (3.18 kDa);

8)    PCNA: SC*AK*DGVK168 (1.02 kDa);

9)    PTEN: MTAIIKEIVSRNK*RRYQED (2.43 kDa);

10)   PTEN: TSEK*VENGSLC*DQEIDSIC*SIERA
      (2.98 kDa).
```

Figure 13:
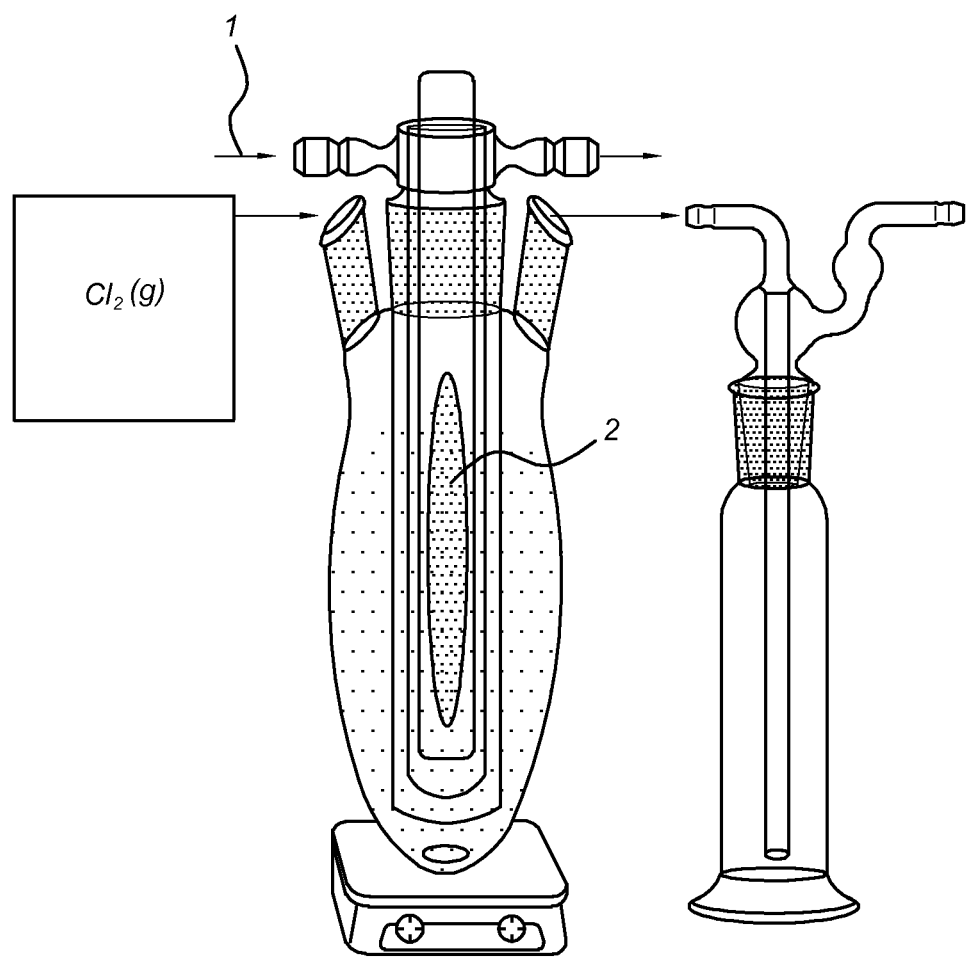

FIG. 13: Experimental setup used for the photochemical chlorination of L(+)-lysine, comprising a CF41 Cryo-Compact Circulator (70° C.) (1) and a Photochemical reactor medium pressure Hg lamp (450 W) (2).

EXAMPLES

General Material and Methods

General reagents were obtained from Sigma Aldrich, Fluka and Acros and used without further purification. H-DL-δ-Hydroxy-DL-Lys-OH.HCl was purchased from Bachem and (5R)-5-hydroxy-L-lysine dihydrochloride monohydrate from Sigma Aldrich. Ubiquitin was purchased from BIOMOL. SUMO proteins 1 and 2, E1 for ubiquitin (UBA) and SUMO (AOS1-SAE2 dimer) were a kind gift from the group of Prof. Titia Sixma (NKI-A V L). V50 (2,2'-Azobis(2-methylpropionamidine) dihydrochloride) was purchased from Sigma Aldrich and VA-044 (2,2'-Azobis[2-(2-imidazolin-2-yl)propane]dihydrochloride) was purchased form Wako Pure Chemical Industries (Japan). Solvents were purchased from BIOSOLVE and Aldrich and dried overnight over molecular sieves (4 Å for DCM, DMF and 3 Å for MeOH) where necessary. Analytical thin layer chromatography was performed on aluminium sheets precoated with silica gel 60 $F_{254}$ using 20% ninhydrin in ethanol and heating by heatgun. Column chromatography was carried out on silica gel (0.035-0.070 mm, 90 Å, Acros). Nuclear magnetic resonance spectra ($^1$H-NMR, 13C-NMR, COSY and HSQC) were determined in deuterated methanol (MeOD-d$_4$, $^1$H reference δ 4.87 ppm; $^{13}$C reference δ 49.15 ppm), deuterated chloroform (CDCl$_3$, $^1$H reference δ 7.26 ppm; $^{13}$C reference δ 77.00 ppm) or deuterated dimethyl sulfoxide (DMSO-d$_6$, $^1$H reference δ 2.50 ppm; $^{13}$C reference δ 39.52 ppm) using a Bruker ARX 400 Spectrometer ($^1$H: 400 MHz, $^{13}$C: 100 MHz) or a Bruker Advance-III 300 Spectrometer ($^1$H: 300 MHz, $^{13}$C: 75 MHz) at 298 K, unless indicated otherwise. Peak shapes in the NMR spectra are indicated with the symbols 'd' (doublet), 'dd' (double doublet), 's' (singlet), 'br s' (broad singlet), T (triplet) and 'm' (multiplet). Chemical shifts (δ) are are given in ppm and coupling constants J in Hz. LC-MS measurements were performed on a system equipped with a Waters 2795 Separation Module (Alliance HT), Waters 2996 Photodiode Array Detector (190-750 nm), Waters Alltima C18 Column (2.1× 100 mm) and an LCT™ Orthogonal Acceleration Time of Flight Mass Spectrometer. Samples were run at a flowrate of 0.40 ml min$^{-1}$ using two mobile phases: A=0.1% aqueous formic acid and B=CH$_3$CN in 0.1% aqueous formic acid.

LC-MS Program 1 (C18 column):

Waters Atlantis T3 C18, 2.1×100 mm, 3 μM); Flow rate=0.4 mL/min, runtime=10 min, column T=20° C., stroke volume=25 μL; Gradient: 0.0⇨ 2.0 min: 5% B; 2.0⇨ 5.0 min: 5% B⇨ 95% B; 5.0⇨ 7.0 min: 95% B; 7.0⇨ 7.2 min: 95% B ⇨ 5% B; 7.2⇨ 9.9 min: 5% B.

LC-MS Program 2 (C4 Column):

Waters Symmetry 300, 2.1×100 mm, 3.5 μM; Flow rate=0.4 mL/min, runtime=24 min, column T=20° C., stroke volume=25 μL; Gradient: 0.0-2.0 min: 5% B; 2.0-20.0 min: 5% B⇨ 90% B; 20.0-21.0 min: 90% B⇨ 95% B; 21.0-24.0 min: 95% B⇨ 5% B.

HPLC (C4, ubiquitin derived compounds):

Shimadzu LC-20AD/T using a C4 Vydac column (Grace Davison Discovery Sciences™, cat #214TP1022). Mobile phases: A=0.05% aqueous TFA and B=CH$_3$CN in 0.05% aqueous TFA. Column T=20° C. Flow rate=10.0 mL/min. Gradient as for LC-MS Program 2.

Example 1

Synthesis δ-thiolysine Building Blocks DL-3.4 and L-3.4

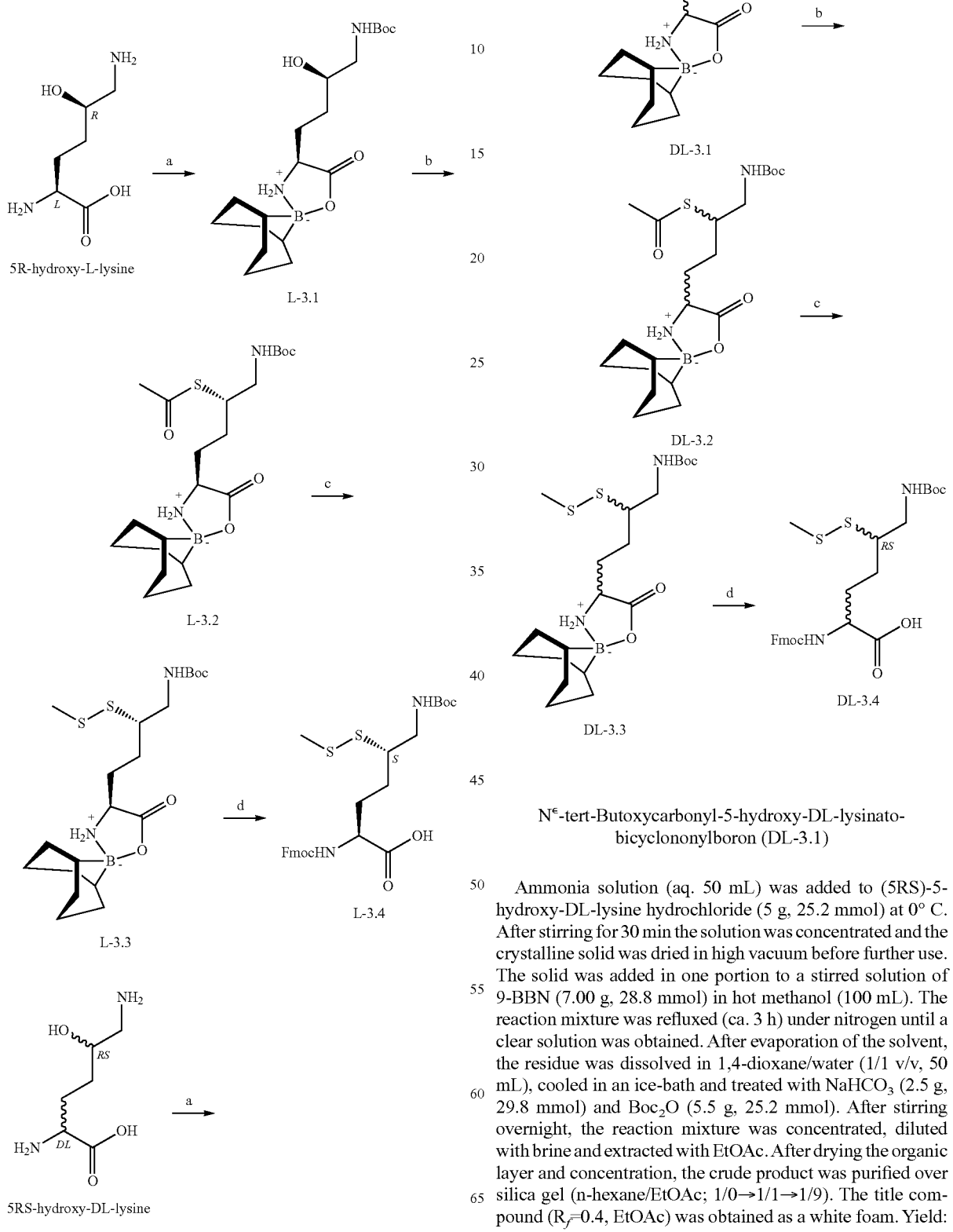

N$^\epsilon$-tert-Butoxycarbonyl-5-hydroxy-DL-lysinato-bicyclononylboron (DL-3.1)

Ammonia solution (aq. 50 mL) was added to (5RS)-5-hydroxy-DL-lysine hydrochloride (5 g, 25.2 mmol) at 0° C. After stirring for 30 min the solution was concentrated and the crystalline solid was dried in high vacuum before further use. The solid was added in one portion to a stirred solution of 9-BBN (7.00 g, 28.8 mmol) in hot methanol (100 mL). The reaction mixture was refluxed (ca. 3 h) under nitrogen until a clear solution was obtained. After evaporation of the solvent, the residue was dissolved in 1,4-dioxane/water (1/1 v/v, 50 mL), cooled in an ice-bath and treated with NaHCO$_3$ (2.5 g, 29.8 mmol) and Boc$_2$O (5.5 g, 25.2 mmol). After stirring overnight, the reaction mixture was concentrated, diluted with brine and extracted with EtOAc. After drying the organic layer and concentration, the crude product was purified over silica gel (n-hexane/EtOAc; 1/0→1/1→1/9). The title compound (R$_f$=0.4, EtOAc) was obtained as a white foam. Yield: >99% over 2 steps.

N$^\epsilon$-tert-Butoxycarbonyl-5R-hydroxy-L-lysinato-bicyclononylboron (L-3.1)

Ammonia solution (aq. 10 mL) was added to (5R)-5-hydroxy-L-lysine dihydrochloride monohydrate (1.04 g, 4.11 mmol) at 0° C. After stirring for 30 min the solution was concentrated and the crystalline solid was dried in high vacuum before further use. The solid was added in one portion to a stirred solution of 9-BBN (1.2 g, 4.7 mmol) in hot methanol (20 mL). The reaction mixture was refluxed (ca. 3 h) under nitrogen until a clear solution was obtained. After evaporation of the solvent, the residue was dissolved in 1,4-dioxane/water (2/3 v/v, 30 mL), cooled in an ice-bath and treated with NaHCO$_3$ (0.5 g) and Boc$_2$O (1.1 g). After stirring overnight, the reaction mixture was concentrated, diluted with brine and extracted with EtOAc. After drying the organic layer and concentration, the crude product was purified over silica gel (n-hexane/EtOAc; 1/0→0/1). The title compound (R$_f$=0.4, EtOAc) was obtained as a white foam. Yield: 1.39 g, 3.63 mmol, 89% over 2 steps. On a 45.7 mmol scale, the product was obtained (silica gel chromatography DCM→10% MeOH/DCM) in an overall yield of 82%. $^1$H-NMR (400 MHz, MeOH/D-d$_4$) δ 3.72-3.59 (m, 2H, H-α and H-δ), 3.12-3.01 (m, 2H, H-ε), 2.11 (m, 1H, H-β), 1.90-1.43 (m, CH-boron, H-β' and H-γ), 1.43 (s, 9H, tBu Boc), 0.57 (d, 2H, CH$_2$ boron, J=16 Hz). $^{13}$C-NMR (100 MHz, MeOD-d4) δ 177.4 (C=O), 158.9 (C=O, Boc), 80.4 (C$_q$ tBu), 71.6 (CH), 56.5 (CH), 47.5 (CH$_2$), 32.7-32.4, 31.7 (CH$_2$), 28.9 (tBu, Boc), 28.4 (CH$_2$), 25.8-25.4 (CH$_2$). LC-MS program 1: R$_t$=6.9 min, MS ES+ (amu): 383.26 [M.H]$^+$, 765.01 [M–M.H]$^+$.

N$^\epsilon$-tert-Butoxycarbonyl-5SR-(S-acetyl)-DL-lysinato-bicyclononylboron (DL-3.2)

Step 1: To a solution of DL-3.1 (0.95 g, 2.48 mmol) and Et$_3$N (730 µL, 5.24 mmol) at 0° C. in dichloromethane (15 mL) was added MsCl (326 µL, 4.19 mmol). The reaction mixture was stirred overnight when TLC analysis revealed no completion. After adding another 0.52 mL of Et$_3$N and 0.23 mL MsCl, the reaction was complete within 1 hr according to TLC analysis. The crude product was purified over silica gel (n-hexane/EtOAc 1/1→1/4) affording the mesylate (R$_f$=0.8, EtOAc) as a foam after drying under high vacuum. Yield: 1.09 g, 2.37 mmol, 95%. LC-MS program 1: R$_t$=7.2 min, MS ES+: 461.19 [M.H]$^+$. $^{13}$C-NMR (100 MHz, MeOD-d4) δ 176.9 (C=O), 158.7 (C=O, Boc), 82.4, 82.2 (CH), 80.7 (C$_q$ tBu), 55.9, 55.8 (CH), 44.7, 44.6 (CH$_2$), 38.6, 36.3 (CH), 32.8, 32.7, 32.5, 32.4 (CH$_2$), 30.4, 30.1 (CH$_2$), 28.9 (tBu, Boc), 27.9, 27.6 (CH$_2$), 25.8, 25.4 (CH$_2$). The reaction was also performed on a 20 mmol scale and the mesylate was isolated in >99% from 5RS-δ-hydroxy-DL-lysine.

Step 2, method using DBU salt of thioacetic acid: A preformed solution of the DBU salt of thioacetic acid, formed by the addition of 5 eq thioacetic acid to a cooled solution of 5 eq DBU in dry DMF (3.5 M), was added to a solution of the mesylate (1.0 eq, 0.45 g, 1.02 mmol) in dry DMF (2 mL). The reaction was stirred overnight at rt when TLC analysis showed complete consumption of starting material and formation of a product spot at R$_f$ 0.6 in n-hexane/EtOAc 1/6. The DMF was evaporated and the concentrate was dissolved in ethyl acetate, washed with brine, dried (MgSO$_4$) and concentrated. The crude product was purified over silica gel (n-hexane→EtOAc 1/3) yielding DL-3.2 as a foam. Yield: >99%.

Step 2, method using potassium thioacetate: Potassium thioacetate (1.75 eq, was added to a solution of the mesylate (1.0 eq, 0.5 g, 1.1 mmol) in dry DMF (7 mL). The reaction was stirred at 65° C. for 2% hrs when TLC analysis showed complete consumption of starting material and formation of a product spot. The DMF was evaporated and the concentrate was dissolved in ethyl acetate, washed with water and brine, dried, and concentrated. Yield after silica gel chromatography: >99%. LC-MS program 1: R$_t$ 7.3 min, MS ES+: 441.51 [M.H]$^+$, 882.46 [M–M.H]$^+$.

N$^\epsilon$-tert-Butoxycarbonyl-5S-(S-acetyl)-L-lysinato-bicyclononylboron (L-3.2)

Step 1: To a solution of L-3.1 (1.35 g, 2.48 mmol) and Et$_3$N (730 µL, 5.24 mmol) at 0° C. in dichloromethane (15 mL) was added MsCl (326 µL, 4.19 mmol). The mixture was stirred for 1 hour when TLC analysis showed completion. The crude product was purified over silica gel (n-hexane/EtOAc 1/1→1/3) affording L-3.1 (R$_f$=0.8, EtOAc) as a foam. Yield: >99%. $^1$H-NMR (400 MHz, MeOD-d4) δ 6.40 (m, 1H), 5.83 (m, 1H), 4.98 (m, 1H), 4.69 (m, 1H), 3.70 (m, 2H, H-α and H-δ), 3.25-3.12 (m, partially obscured by MeOD-d4 peak), 2.69 (s, 3H), 2.11 (m, 1H, H-β), 2.12-1.30 (m, CH-boron, H-β and H-γ), 1.20 (s, 9H, tBu Boc), 0.57 (broad s, 2H, CH$_2$ boron). LC-MS program 1: R$_t$=7.3 min, MS ES+ (amu): 461.19 [M.H]$^+$, 920.77 [M–M.H]$^+$.

Step 2, method using DBU salt of thioacetic acid: A preformed solution of the DBU salt of thioacetic acid, formed by the addition of thioacetic acid (5 eq) to a cooled solution of DBU (5 eq) in dry DMF (3.5 M), was added to a solution of the mesylate (1 eq) in dry DMF (2 mL). The reaction was stirred overnight at rt when TLC analysis showed incomplete consumption of starting material. Another 2.5 eq of fresh DBU·HSAc was added. The reaction was left stirring overnight. The DMF was evaporated and the concentrate was dissolved in ethyl acetate, washed with water and brine, dried, and concentrated. The crude product was purified over silica gel (n-hexane→EtOAc 1/3) yielding L-3.2 as a foam. Yield: 1.13 g, >99%.

Step 2, method using potassium thioacetate: KSAc (1.75 eq, 10.9 mmol, 1.25 g) was added to a solution of the mesylate (1.0 eq, 2.87 g, 6.23 mmol) in dry DMF (58 mL). The reaction was stirred at 65° C. for 3 hrs when TLC and LC-MS analysis showed completion. The DMF was evaporated and the concentrate was dissolved in EtOAc, washed with water and brine, dried, and concentrated. Yield after silica gel chromatography: 2.21 g, 5.05 mmol, 81%. $^1$H-NMR (400 MHz, MeOD-d4) δ 3.64 (app dd, 2H, H-α and H-δ, J=4.8 and 8.5 Hz), 3.55 (dd, 1H, H-ε, J=5.8 and 14.2 Hz), 3.12 (dd, 1H, H-ε', J=7.3 and 14.1 Hz), 2.33 (s, 3H), 2.10-1.30 (m, CH-boron, H-β and H-γ), 1.43 (s, 9H, tBu Boc), 0.57 (broad s, 2H, CH$_2$ boron). $^{13}$C-NMR (100 MHz, MeOD-d4) δ 197.0 (C=O SAc), 177.1 (C=O), 158.8 (C=O, Boc), 80.5 (C$_q$ tBu), 55.9 (CH), 45.7 (CH$_3$), 45.1 (CH$_2$), 32.8, 32.7, 32.4 (4×CH$_2$), 30.9 (CH), 29.6, 29.3 (2×CH$_2$), 28.9 (tBu, Boc), 28.4 (CH$_2$), 25.8, 25.4 (2×CH$_2$). LC-MS program 1: R$_t$=7.4 min, MS ES+ (amu): 441.28 [M.H]$^+$, 880.97 [M–M.H]$^+$.

N$^\epsilon$-tert-Butoxycarbonyl-5-(methyldisulfanyl)-lysinato-bicyclononylboron (DL-3.3)

Thioacetate DL-3.2 (1.00 g, 2.27 mmol) was dissolved in methanol (15 mL) and treated with a 1N NaOH solution (3 mL) for 15 min at 0° C. The reaction mixture was carefully neutralized by the addition of equimolar amounts of HOAc and concentrated. The concentrate was dissolved in ethyl acetate and washed with water and brine, dried (MgSO$_4$), and concentrated affording the crude thiol as an oil. Next, a solution of the crude thiol in DCM (7 mL) was added dropwise to a solution of S-Methyl methanethiolsulfonate (3 equiv, 6.9 mmol, 0.66 mL) and Et$_3$N (9 equiv, 2.76 mL, 20.4 mmol) in DCM (7 mL). The reaction mixture was stirred for 1 h after which TLC analysis (n-hexane/EtOAc 1/3) showed complete consumption of starting material. After evaporation of the DCM, the crude product was purified over silica gel (n-hexane→EtOAc 2/3) affording disulfide DL-3.3 (R$_f$=0.8, EtOAc) as a yellow oil. Yield: 0.99 g, 2.23 mmol, 98% over 2 steps. Reaction on a 7.9 mmol scale gave DL-3.3 in 90% over 2 steps. LC-MS program 1: R$_t$=7.5 min, MS ES+ (amu): 445.47 [M.H]$^+$, 889.43 [M–M.H]$^+$.

N$^\epsilon$-tert-Butoxycarbonyl-5S-(methyldisulfanyl)-L-lysinato-bicyclononylboron (L-3.3)

Thioacetate L-3.2 (1.13 g, 2.5 mmol) was dissolved in methanol (15 mL) and treated with 1N NaOH solution (3 mL) for 15 min at 0° C. The reaction mixture was carefully neutralized by the addition of equimolar amounts of HOAc and concentrated. The concentrate was dissolved in ethyl acetate and washed with water and brine, dried (MgSO$_4$), and concentrated affording the crude thiol as an oil. $^1$H-NMR (400 MHz, MeOD-d4) δ 3.64 (app t, 1H, H-α J=7.5 and 5.4 Hz), 3.28 (dd, 1H, H-ε, J=7.6 and 14.1 Hz), 3.13 (dd, 1H, H-ε', J=6.8 and 13.9 Hz), 2.87 (broad s, 1H, H-δ), 2.10-1.30 (m, CH-boron, H-β and H-γ), 1.43 (s, 9H, tBu Boc), 0.57 (broad d, 2H, CH$_2$ boron, J=13.9 Hz). $^{13}$C-NMR (100 MHz, MeOD-d4) δ 177.3 (C=O), ≈159 (C=O, Boc, low intensity peak), 80.5 (C$_q$ tBu), 56.2 (CH), 49.1 (CH$_2$, partially obscured by MeOD-d4), 41.5 (CH), 33.1, 32.8, 32.7, 32.5, 32.4, 29.7 (5×CH$_2$), 29.0 (CH), 28.9 (tBu, Boc), 25.8, 25.4 (2×CH$_2$). Next, a solution of the crude thiol in DCM (7 mL) was added dropwise to a solution of S-Methyl methanethiolsulfonate (3 equiv, 6.9 mmol, 0.66 mL) and Et$_3$N (9 equiv, 2.76 mL, 20.4 mmol) in DCM (7 mL). The reaction mixture was stirred for 1 h after which TLC analysis (n-hexane/EtOAc 1/3) showed complete consumption of starting material. After evaporation of the DCM, the crude product was purified over silica gel (n-hexane→EtOAc 2/3) affording disulfide L-3.3 (R$_f$=0.8, EtOAc) as an oil. Yield: 1.1 g, 2.5 mmol, >99% over 2 steps. $^1$H-NMR (400 MHz, MeOD-d4) δ 3.68 (dd, 1H, H-α, J=5.4 and 6.8 Hz), 3.29 (m, 2H, H-ε, obscured by MeOD-d4 peak), 2.89 (m, 1H, H-δ), 2.43 (s, 3H, SMe), 1.90-1.43 (m, CH-boron, H-β and H-γ), 1.45 (s, 9H, tBu Boc), 0.58 (broad d, 2H, CH$_2$ boron, J=12.3 Hz). $^{13}$C-NMR (100 MHz, MeOD-d4) δ 177.1 (C=O), 158.7 (C=O, Boc), 80.5 (C$_q$ tBu), 56.1, 52.7, 48.9 (3×CH), 45.0 (CH$_2$), 32.8, 32.7, 32.4, 29.6, 29.1 (6×CH$_2$), 28.9 (tBu, Boc), 25.8, 25.4 (2×CH$_2$), 24.5, 18.5 (2×CH).

N$^\alpha$-(Fluoren-9-ylmethoxycarbonyl)-M-tert-Butoxycarbonyl-5-(methyldisulfanyl)-DL-lysine (DL-3.4)

Compound DL-3.3 (2.6 g, 5.9 mmol) was dissolved in THF (40 mL) and ethylene diamine (3.0 mL) was added. The solution was heated to −70° C. for 5 min when a white solid precipitated. The reaction mixture was filtered over Hyflo® and the filtrate was purified by flash column chromatography (DCM⇒ 40% MeOH in DCM, R$_f$=0.4). affording the free amino acid as an oil. $^{13}$C-NMR (100 MHz, MeOD-d4) δ 177.3 (C=O), 158.6 (C=O, Boc), 80.4 (C$_q$ tBu), 56.1 (2×CH), 52.9 (CH), 50.0 (CH), 45.3 (2×CH$_2$), 30.1 (CH$_2$), 28.9 (tBu, Boc), 28.9, 28.4 (CH$_2$), 24.5 (CH). LC-MS program 1: R$_t$=5.6 min, MS ES+ (amu): 325.25 [M.H]$^+$, 649.11 [M–M.H]$^+$. Next, a solution of Fmoc-OSu (2.5 g, 7.4 mmol) in acetone (25 mL) was added to a solution of the crude amino acid and NaHCO$_3$ (0.59 g, 1.1 eq) in acetone/H$_2$O (50 mL/50 mL). The reaction mixture was stirred overnight at room temperature, concentrated, acidified with 1N aq. HCl and extracted with DCM. The aqueous layer was extracted again with chloroform and EtOAc. The combined organic layers were dried (MgSO$_4$) and concentrated under reduced pressure. The residue was purified by flash column chromatography (10% MeOH in DCM). Yield: 1.5 g, 2.7 mmol, 46% over 2 steps. $^{13}$C-NMR (100 MHz, MeOD-d4) δ low intensity for C=O peak, 157.2 (C=O, Boc), 144.0, 143.8, 141.2 (C$_q$ Fmoc), 127.4, 126.8, 124.9, 119.5 (CH Fmoc), 78.8 (C$_q$ tBu), 66.6 (CH$_2$), 51.2, 50.9 (2×CH), 48.4, 47.0 (2×CH), 43.8 (2×CH$_2$), 29.3, 29.1, 27.6 (3×CH$_2$), 27.4 (tBu, Boc), 27.3 (CH$_2$), 23.0 (CH). LC-MS program 1: R$_t$=7.5 min, MS ES+ (amu): 547.14 [M.H]$^+$.

N$^\alpha$-(Fluoren-9-ylmethoxycarbonyl)-N$^\epsilon$-tert-Butoxycarbonyl-5S-(methyldisulfanyl)-L-lysine (L-3.4)

Compound L-3.3 (1.15 g, 2.5 mmol) was dissolved in THF (40 mL) and ethylene diamine (1.3 mL) was added. The solution was heated to −70° C. for 5 min when a white solid precipitated. The precipitate was removed by centrifugation in a Falcon tube (10 min at 4000 rpm) or by filtration over Hyflo®. The filtrate was concentrated and purified by flash column chromatography (DCM→40% MeOH in DCM, R$_f$=0.4). Yield: 0.54 g, 1.67 mmol, 67%, oil. LC-MS program 1: R$_t$=5.7 min, MS ES+ (amu): 325.40 [M.H]$^+$, 649.39 [M–M.H]$^+$. Next, a solution of Fmoc-OSu (1.25 eq, 0.66 g, 2.0 mmol) in acetone (10 mL) was added to a solution of this amino acid (0.51 g, 1.57 mmol) and NaHCO$_3$ (145 mg, 1.73 mmol, 1.1 eq) in acetone/H$_2$O (10 mL/10 mL). The reaction mixture was stirred overnight at room temperature, concentrated, acidified with 1N aq. HCl and extracted with EtOAc. The organic layer was dried (MgSO$_4$) and concentrated under reduced pressure. The residue was purified by flash column chromatography (10% MeOH in DCM). Yield: 441 mg, 0.81 mmol, 51%, foam. $^1$H-NMR (400 MHz, MeOD-d4) δ 7.75 (d, 2H, Fmoc, J=7.5 Hz), 7.64 (t, 2H, Fmoc, J=6.5 Hz), 7.37 (t, 2H, Fmoc, J=7.3 Hz), 7.29 (double t, 2H, Fmoc, J=1.2, 7.4 and 7.5 Hz), 4.31 (d, 2H, J=6.6 Hz), 4.18 (t, 1H, J=6.9 Hz), 4.12 (dd, 1H, 4.8 and 8.2 Hz), 3.18 (m, 1H), 2.79 (m, 1H), 2.35 (s, SMe), 2.15 (m, 1H), 1.92 (m, 1H), 1.73 (m, 1H), 1.59 (m, 1H), 1.40, 1.38 (s, tBu Boc). $^{13}$C-NMR (100 MHz, MeOD-d4) δ 176.9 (C=O), 158.7 (C=O, Boc), 145.5, 145.3, 142.7 (C$_q$ Fmoc), 128.9, 128.3, 126.4, 121.0 (CH Fmoc), 80.4 (C$_q$ tBu), 68.1 (CH$_2$), 55.7, 52.4 (2×CH), 48.5 (CH), 45.5 (CH$_2$), 30.6, 28.8 (2×CH$_2$), 28.9 (tBu, Boc), 24.5 (CH). LC-MS program 1: R$_t$=7.5 min, MS ES+ (amu): 547.18 [M.H]$^+$.

Example 2

Solid Phase Synthesis of Peptides Modified with DL-3.4 and (O-Nitrobenzyl)-Cysteine Peptides were synthesized on a Syro II MultiSyntech Automated Peptide synthesizer by standard 9-fluorenylmethoxycarbonyl (Fmoc-) based solid phase peptides chemistry on a 25 or 50 μmol. Starting with the pre-loaded Fmoc amino acid Wang resin (0.2 mmol/g), each successive amino acid was coupled in 4 molar excess for 45 min with pyBOP and DiPEA. Deprotection of the Fmoc-group was achieved with 20% piperidine in NMP (3×1.2 mL, 2×2 and 1×5 min). Peptides were cleaved with TFA/iPr$_3$SiH/H$_2$O (95/2.5/2.5) and precipitated in cold n-hexane/diethyl ether. Purifications were performed on a Waters 1525EF Binary HPLC using an Atlantis (Waters, 19×250 mm, 10 μM) preparative column. Flow rate=1.4 mL/min, mobile phases: A=0.05% aq. TFA and B=CH$_3$CN in 0.05% aq. TFA. Column T=20° C. Gradient: 0.0-1.0 min: 1% B; 1.0-11.0 min: 1% B⇒90% B; 11.0-14.0 min: 90% B; 14.0-15.0 min: 90% B⇒95% B; 15.0-23.0 min: 1% B.

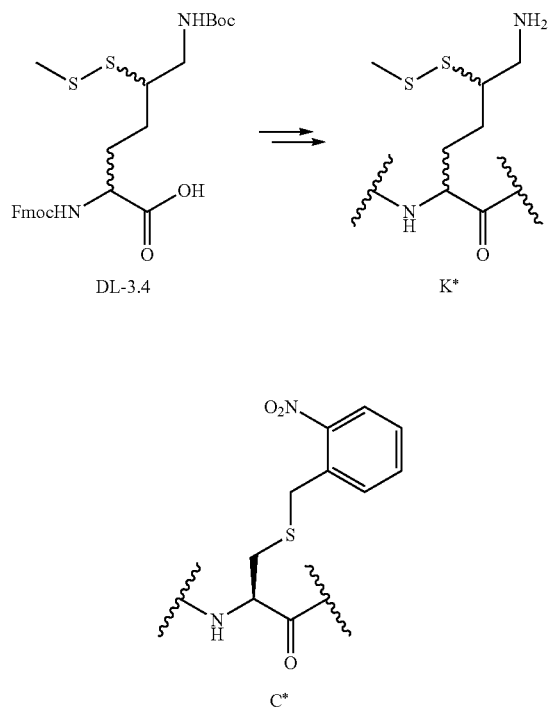

Example 3

Site- and Chemoselective Ubiquitination of Peptides Using the Traceless Lysine Building Block δ-Thiolysine General Protocol Ubiquitin Ligation of 5-Thiolysine Modified Peptides.

Stock solutions reagents:
- 200 mM MgCl$_2$
- 0.5 M ATP
- 2.0 M MESNa
- 10 mg mL ubiquitin in 50 mM Tris-HCl (pH 7.5)
- 71 μM E1 and 7.1 μM (by diluting first stock 10×) in milliQ Stock Solutions Peptides:
- (0) Peptide TKAVTK*YTSSK: 20 mM in milliQ or 50 mM Tris-HCl (pH 7.5)
- (1) [155]GDAWISC*AK*DGVKFSASGELGNGNIKLSQ[184]: 5.0 mM in DMF or DMSO
- (2) [161]SC*AK*DGVK[168]: 500 μM in 50 mM Tris-HCl (pH 7.5)
- (3) [1]MTAIIKEIVSRNK*RRYQED[19]: 500 μM in 50 mM Tris-HCl (pH 7.5)
- (4) [286]TSEK*VENGSLC*DQEIDSIC*SIERA[399]: 500 μM in 50 mM Tris-HCl (pH 7.5)
- (5) [365]HLK*SKKGQSTSRHKKLMFKTEG[389]: 1000 μM in 50 mM Tris-HCl (pH 7.5)
- (6) [365]HLKSK*KGQSTSRHKKLMFKTEG[389]: 1000 μM in 50 mM Tris-HCl (pH 7.5)
- (7) [365]HLKSKK*GQSTSRHKKLMFKTEG[389]: 1000 μM in 50 mM Tris-HCl (pH 7.5)
- (8) [365]HLKSKKGQSTSRHK*KLMFKTEG[389]: 1000 μM in 50 mM Tris-HCl (pH 7.5)
- (9) [365]HLKSKKGQSTSRHKK*LMFKTEG[389]: 1000 μM in 50 mM Tris-HCl (pH 7.5)

TABLE 1

| Analysis Peptides modified with DL-3.4 and (o-nitrobenzyl)-cysteine. | | | |
|---|---|---|---|
| Peptide | Mol Weight (Da) | MS ES+ found (amu) | Rt (min) |
| TKAVTKYTSSK | 1213 | 1214.2 (M · H)$^+$ | 9.7 |
| TKAVTK*YTSSK | 1290 | 1291.8 (M · H)$^+$ | 11.3 |
| GDAVVISC*AK*DGVKFSASGELGNGNIKLSQ | 3179 | 1588.8 (M · 2H)$^{2+}$ | 11.0 |
| SC*AK*DGVK | 1021 | 1019.9 (M · H)$^+$ | 9.9 |
| TSEK*VENGSLC*DQEIDSIC*SIERA | 2975 | 1487.3 (M · 2H)$^{2+}$ | 11.9 |
| MTAIIKEIVSRNK*RRYQED | 2430 | 1214.6 (M · 2H)$^{2+}$ | 10.3-10.6 |
| HLK*SKKGQSTSRHKKLMFKTEG | 2636 | 1317.1 (M · 2H)$^{2+}$ | 9.3-9.4 |
| HLKSK*KGQSTSRHKKLMFKTEG | 2636 | 1317.1 (M · 2H)$^{2+}$ | 9.3 |
| HLKSKK*GQSTSRHKKLMFKTEG | 2636 | 1317.1 (M · 2H)$^{2+}$ | 9.3 |
| HLKSKKGQSTSRHK*KLMFKTEG | 2636 | 1317.1 (M · 2H)$^{2+}$ | 9.4 |
| HLKSKKGQSTSRHKK*LMFKTEG | 2636 | 1317.1 (M · 2H)$^{2+}$ | 9.5 |
| HLKSKKGQSTSRHKKLMFK*TEG | 2636 | 1317.6 (M · 2H)$^{2+}$ | 9.5 |

(10) ³⁶⁵HLKSKKGQSTSRHKKLMFK*TEG³⁸⁹: 1000 μM in 50 mM Tris-HCl (pH 7.5)
Standard Reaction Mixture in 50 mM Tris-HCl (pH 7.5):
4 mM MgCl₂
50 mM MESNa
ubiquitin
peptide
2 mM ATP
E1

Reaction incubated at 37° C. for >6 hrs, sample diluted in NuPAGE® LDS sample buffer (3×, Invitrogen), heated at 71° C. for 10 minutes and loaded on 12% NuPAGE® Novex® Bis-Tris Mini Gels (Invitrogen) using MES SDS running buffer (V=200V). As marker was used the BenchMark™ Pre-Stained Protein Ladder (FIG. 1, Invitrogen)

General Protocol for Metal-Free Desulfurization.

A 0.5 mM solution of peptide in milliQ (400 μL) was incubated overnight at 37° C. with:
100 μL of a 40 mM glutathione solution
80 μL of a 0.2 M VA-044 or V-50 solution (see the structures below)
400 μL of a 0.2 M sodium phosphate buffer (pH=6.5) containing 0.5 M TCEP.

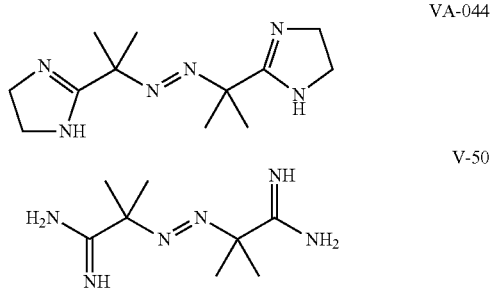

Ub Ligation on H₂B(115-125) Peptide TKAVTKYTSSK Modified with Thiolysine Building Block DL-3.4.

In order to evaluate the efficiency of the here presented thiolysine building block in the ubiquitination of a peptide we choose to incorporate DL-3.4 in the peptide used by Muir and co-workers (*Angew. Chem. Int. Ed.* 2007, 46, 2814), TKAVTK*YTSSK. This sequence corresponds to residues 115-125 of the histone nucleoprotein H₂B with the italic K* indicating the position of the thiolysine residue. Furthermore, we decided to use the natural alanine residue at position 117 in contrast to Muir and co-workers (*Nature,* 2008, 453, 812) who replaced this with cysteine as a potential site for thiol conjugation. Based on the protocol by Balakirev and co-workers (*ChemBiochem,* 2006, 7, 1667) the present inventors performed a set of experiments during which it was determined after how many hours complete ligation of ubiquitin to the peptide was observed (FIG. 2), the minimal amount of peptide (FIG. 3) and E1 concentration (FIG. 4). The ligation reaction mixture was incubated at 37° C. and consisted of the following ingredients: 50 mM Tris.HCl buffer (pH 7.5), 50 mM MESNa, 4 mM ATP, 2 mM MgCl₂, E1, Ub and TKAVTK*YTSSK. Reactions were analysed by SDS-PAGE and LC-MS.

Figure 5:
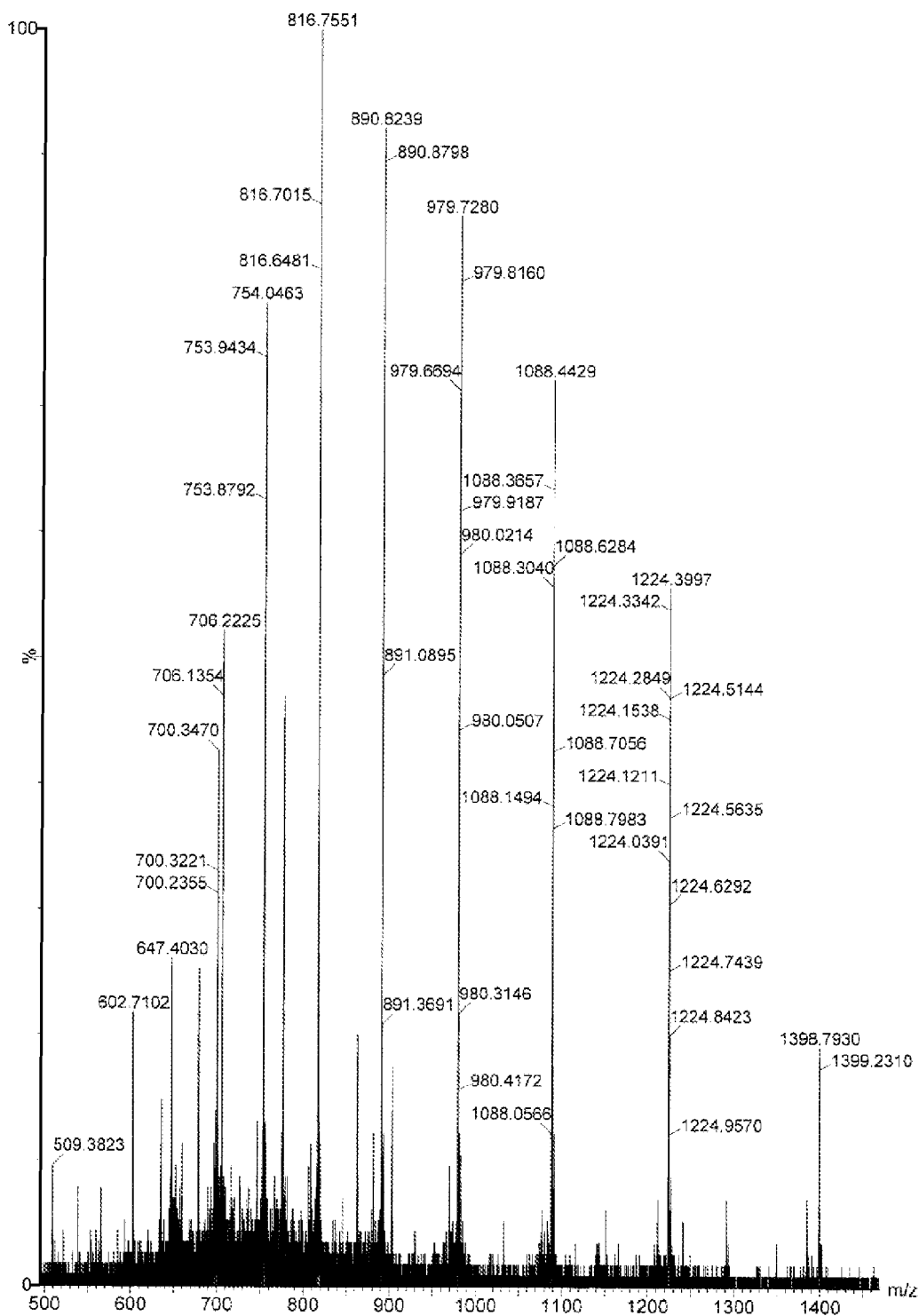
FIG. 5: $ES^+$ spectrum of formation ligation product after treatment of disulfide intermediate with TCEP.

The results in FIGS. 2-4 show that the Ub ligation is fast (complete conversion in <4 hours), requires low nM concentrations of E1 (15 nM) and >10 equiv. of peptide for full conversion of ubiquitin (within this timeframe). When MESNa was replaced for TCEP no ligation was observed, which supports the earlier observation by Balakirev and co-workers that the MESNa thioester is the reactive species. As expected, when the 5-thiolysine building block was replaced by a native lysine (thus employing the peptide TKAVT-KYTSSK) no ligation took place. Overall it was established that the use of the thiolysine based peptide resulted in a very efficient and economical ligation of ubiquitin. LC-MS and MALDI analysis showed that a ligation product was formed which had a mass of 9.93 kDa, corresponding to the asymmetrical disulfide of the expected ligation product (mass 9.79 kDa) and mercaptoethanesulfonic acid (0.14 kDa). When an LC-MS sample was prepared in 0.5 M TCEP in sodium phosphate buffer pH 6.5, the reduced ligation product was observed (FIG. 5). A (HPLC) purified sample of the ligation product was subjected to a selective thiol desulfurization protocol based on the use of thermolabile free radical initiators VA-044 and V-50. Thus, when an aq. solution of TKAVTK*(Ub)YTSSK was incubated overnight at 37° C. with glutathione (hydrogen source), VA-044 or V-50 and TCEP in sodium phosphate buffer (pH 6.5), the desulfurized product was formed according to LC-MS and MALDI analysis.

Ub Ligation on δ-Thiolysine Peptides Derived from PCNA, PTEN and p53.

Building block DL-3.4 was subsequently incorporated in a set of peptides derived from three biologically relevant monoubiquitinated proteins (Table 1). Peptides 1 and 2, respectively, correspond to residues 155-184 and 161-168 of PCNA (Proliferating Cell Nuclear Antigen), a processivity factor for DNA polymerases. Building block DL-3.4 (K*) was incorporated at position 164 which is a conserved (yeast and mammalian) monoubiquitinated lysine residue. Peptides 3 and 4, respectively, correspond to residues 1-19 and 286-309 of the tumor suppressor PTEN (Phosphatase and tensin homolog on chromosome TEN). DL-3.4 was incorporated at position 13 and 289 which have been shown to be two major monoubiquitinated sites of PTEN, regulating its nuclear import. As all four peptide sequences contain a cysteine residue we chose to incorporate it as S-(o-nitrobenzyl) cysteine (C*, Table 1) as the nitrobenzyl group should be compatible with the ligation conditions and is easily removed by photolysis. Finally DL-3.4 was incorporated in a p53 sequence corresponding to residues 365-389 of its C-terminal regulatory part. It is interesting to note that C-terminal p53 peptides have been shown to enhance radiation-induced apoptosis in human mutant p53 cancer cells. As all 6 lysine residues in this sequence are known to be ubiquitination sites, a set of 6 peptides were synthesised.

Figure 6:
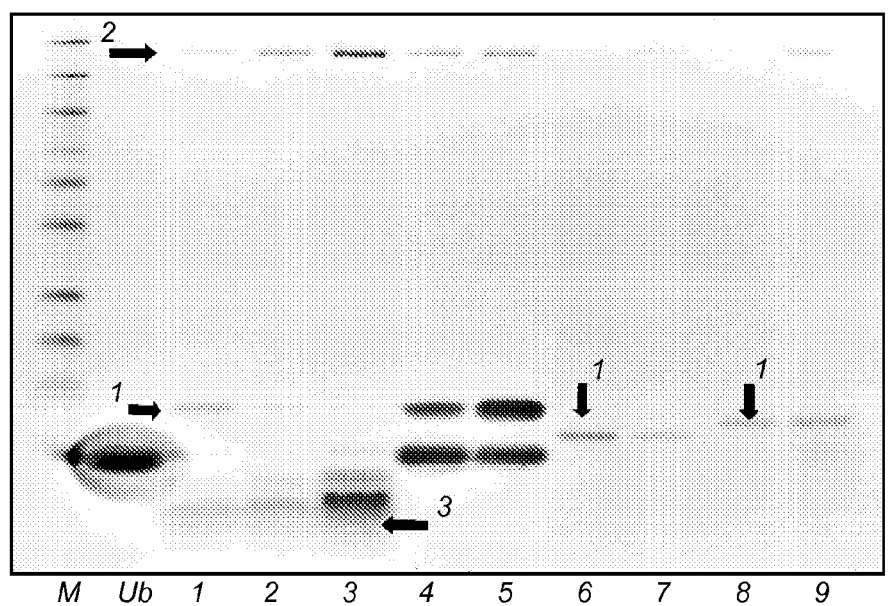
FIG. 6: SDS-PAGE (12%) analysis ubiquitin ligation of peptides 1-3. Reagents and conditions: 50 mM Tris-HCl buffer pH 7.5+4 mM $MgCl_2$+2 mM ATP+50 mM MESNa; overnight incubation at 37° C. 1=5 µM Ub+250 µM Peptide 1 (DMF, 5%)+150 nM E1; 2=5 µM Ub+500 µM Peptide 1 (DMSO, 10%)+300 nM E1; 3=5 µM Ub+500 µM Peptide 1 (DMF, 10%)+300 nM E1; 4=33 µM Ub+45 µM Peptide 1 (DMSO, 1%)+300 nM E1; 5=33 µM Ub+45 µM Peptide 1 (DMF, 1%)+300 nM E1; 6=5 µM Ub+250 µM Peptide 2+150 nM E1; 7=5 µM Ub+500 µM Peptide 3+300 nM E1; 8=5 µM Ub+250 µM Peptide 3+150 nM E1; 9=5 µM Ub+500 µM Peptide 3+300 nM E1. $^1\rightarrow$=ligation product; $^2\rightarrow$=E1, $^3\rightarrow$=peptide (residues).
Figure 7:
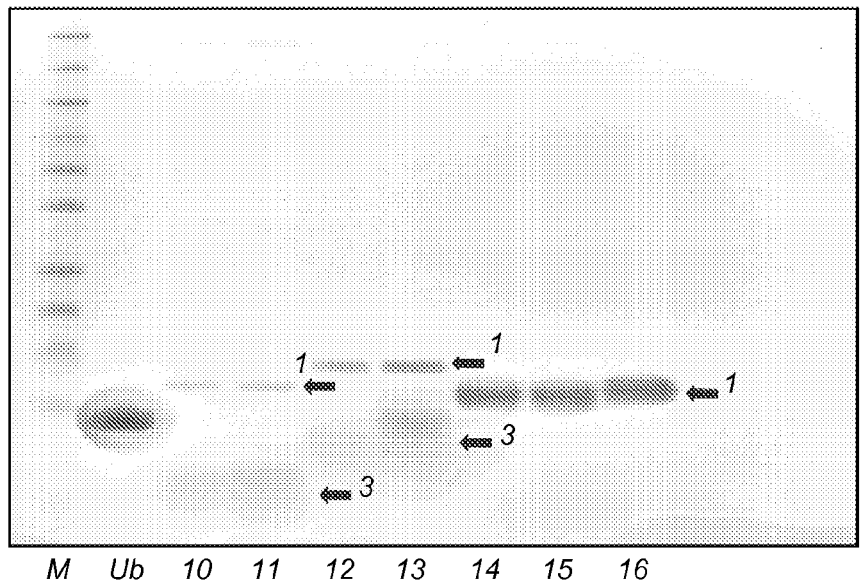
FIG. 7: SDS-PAGE ubiquitin ligation of peptides 4, 5 and TKAVTK*YTSSK. Reagents and conditions: 50 mM Tris-HCl buffer pH 7.5+4 mM $MgCl_2$+2 mM ATP+50 mM MESNa; overnight incubation at 37° C. 10=5 µM Ub+250 µM Peptide 4+150 nM E1; 11=5 µM Ub+500 µM Peptide 4+300 nM E1; 12=5 µM Ub+250 µM Peptide 5+150 nM E1; 13=5 µM Ub+500 µM Peptide 5+300 nM E1; 14=25 µM Ub+250 µM TKAVTK*YTSSK+150 nM E1; 15=25 µM Ub+250 µM TKAVTK*YTSSK (DMSO, 1.25%)+150 nM E1; 16=25 μM Ub+250 μM TKAVTK*YTSSK (DMSO, 10%)+150 nM E1. $^1\rightarrow$=ligation product; $^3\rightarrow$=peptide (residues).
Figure 8:
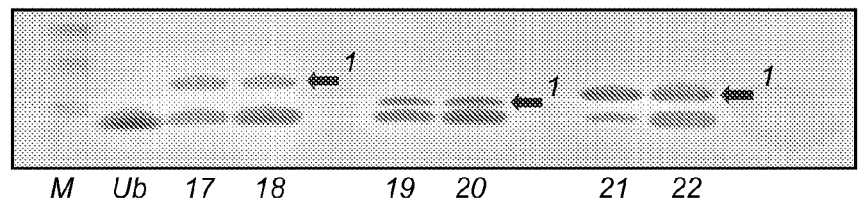
FIG. 8: SDS-PAGE ubiquitin ligation of peptides 1-10—Part II. Reagents and conditions: 50 mM Tris-HCl buffer pH 7.5+4 mM MgCl$_2$+2 mM ATP+50 mM MESNa+250 nM E1; overnight incubation at 37° C. 17=50 μM Ub+50 μM Peptide 1; 21=50 μM Ub+50 μM Peptide 3; 18=100 μM Ub+50 μM Peptide 1; 22=100 μM Ub+50 μM Peptide 3; 19=50 μM Ub+50 μM Peptide 2; 20=100 μM Ub+50 μM Peptide 2. $^1\rightarrow$=ligation product.
Figure 9:
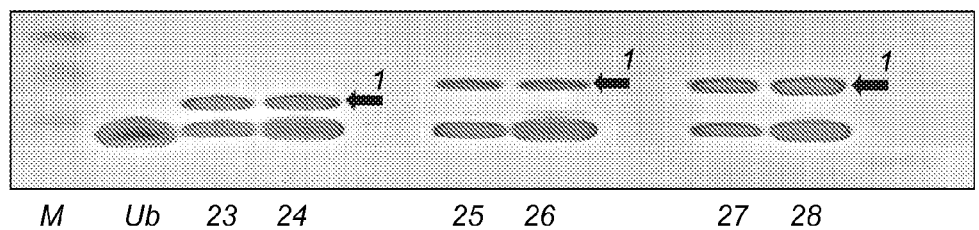
FIG. 9: SDS-PAGE ubiquitin ligation of peptides 1-10—Part II. Reagents and conditions: 50 mM Tris-HCl buffer pH 7.5+4 mM MgCl$_2$+2 mM ATP+50 mM MESNa+250 nM E1; overnight incubation at 37° C. 23=50 μM Ub+50 μM Peptide 4 27=50 μM Ub+50 μM Peptide 6; 24=100 μM Ub+50 μM Peptide 4 28=100 μM Ub+50 μM Peptide 6; 25=50 μM Ub+50 μM Peptide 5; 26=100 μM Ub+50 μM Peptide 5. $^1\rightarrow$=ligation product.
Figure 10:
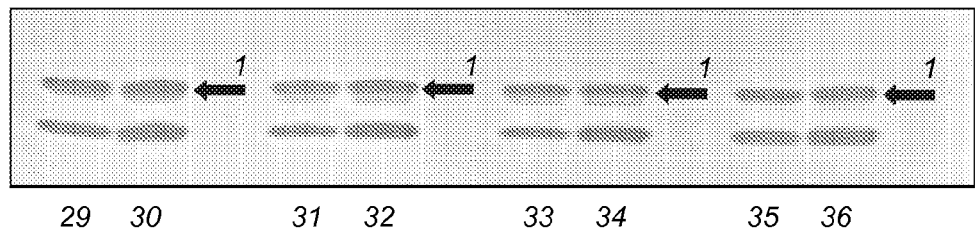
FIG. 10: SDS-PAGE ubiquitin ligation of peptides 1-10—Part II. Reagents and conditions: 50 mM Tris-HCl buffer pH 7.5+4 mM MgCl$_2$+2 mM ATP+50 mM MESNa+250 nM E1; overnight incubation at 37° C. 29=50 μM Ub+50 μM Peptide 7 33=50 μM Ub+50 μM Peptide 9; 30=100 μM Ub+50 μM Peptide 7 34=100 μM Ub+50 μM Peptide 9; 31=50 μM Ub+50 μM Peptide 8 35=100 μM Ub+50 μM Peptide 10; 32=50 μM Ub+50 μM Peptide 8 36=100 μM Ub+50 μM Peptide 10. $^1\rightarrow$=ligation product.

Peptides 2-10 were found to be soluble in the Tris-HCl pH 7.5 buffer used during the ligation reaction. Peptide 1 however, proved to be only soluble in polar organic solvents such as DMF and DMSO. This is not surprising as this peptide is made up for ≈50% of hydrophobic amino acids and contains 3 beta-strands in the native PCNA protein (see Supporting Information). Besides performing the ubiquitin ligations with an excess of peptide (rxn 1-3 and 6-16, FIGS. 6 and 7), it was also observed that the use of (roughly) equimolar amounts of ubiquitin and peptide (rxn 4, 5 FIG. 6 and FIGS. 8-10) allowed ligation. In order to be able to develop the here presented ligation methodology for solid phase peptide synthesis, with the peptide being anchored to the solid support, it is important to fully consume all peptide. In order to confirm that a polar organic solvent is compatible with the reaction conditions, we repeated the ubiquitin ligation of the H₂B peptide TKAVTK*YTSSK, using a DMSO stock of the peptide, up to a final concentration of 10% DMSO (rxn 14-16, FIG. 7). As seen with rxn 1-5 (FIG. 6), DMSO did not have a negative effect on the ubiquitin ligation reaction.

Figure 11:
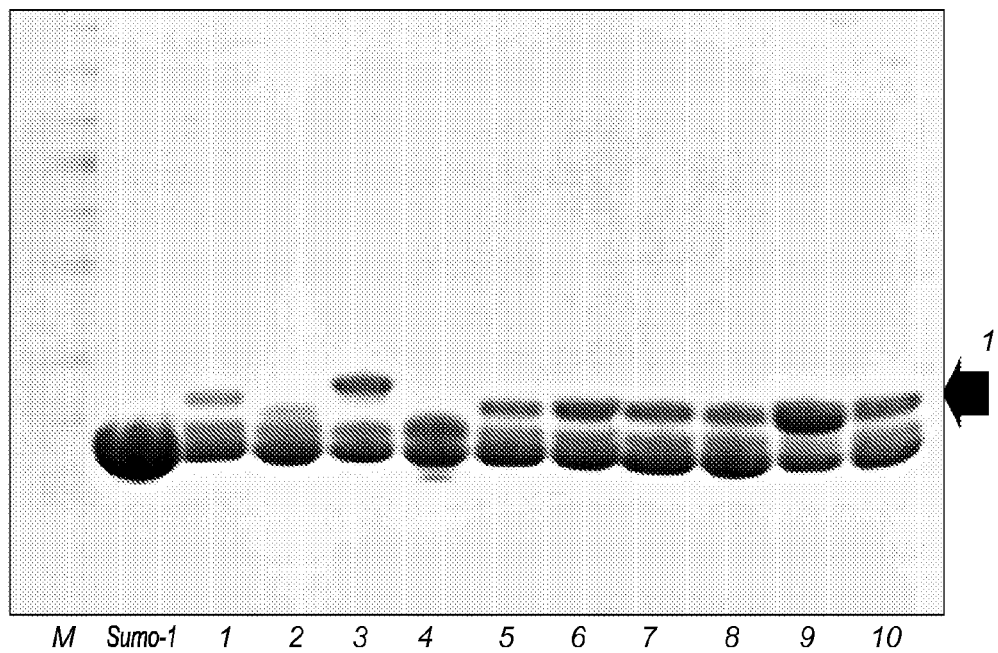
FIG. 11+12: SDS-PAGE SUMO-1 and 2 ligation of peptides 1-10 (50 μM, 1 equiv). Reagents and conditions: 50 mM Tris.HCl buffer pH 7.5+4 mM MgCl$_2$+2 mM ATP+50 mM MESNa+100 μM SUMO-1 or SUMO-2 (2 equiv based on peptide)+250 nM SUMO E1; overnight incubation at 37° C. $^1\rightarrow$=ligation product.
Figure 12:
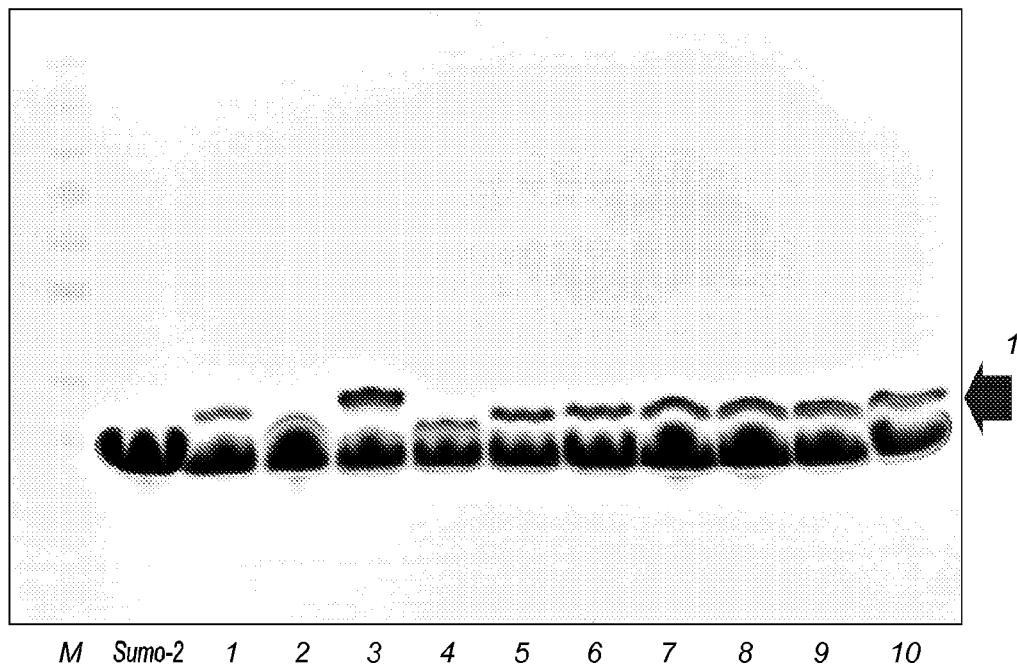

To demonstrate the generality of our approach for conjugating ubiquitin-like proteins (Ubl), peptides 1-10 (Table 1) were also ligated with SUMO-1 (FIG. 11) and SUMO-2 (FIG. 12) using 250 nM SUMO E1 (Aos1-SAE2 dimer).

Example 4

Synthesis γ-Thiolysine Building Block 4

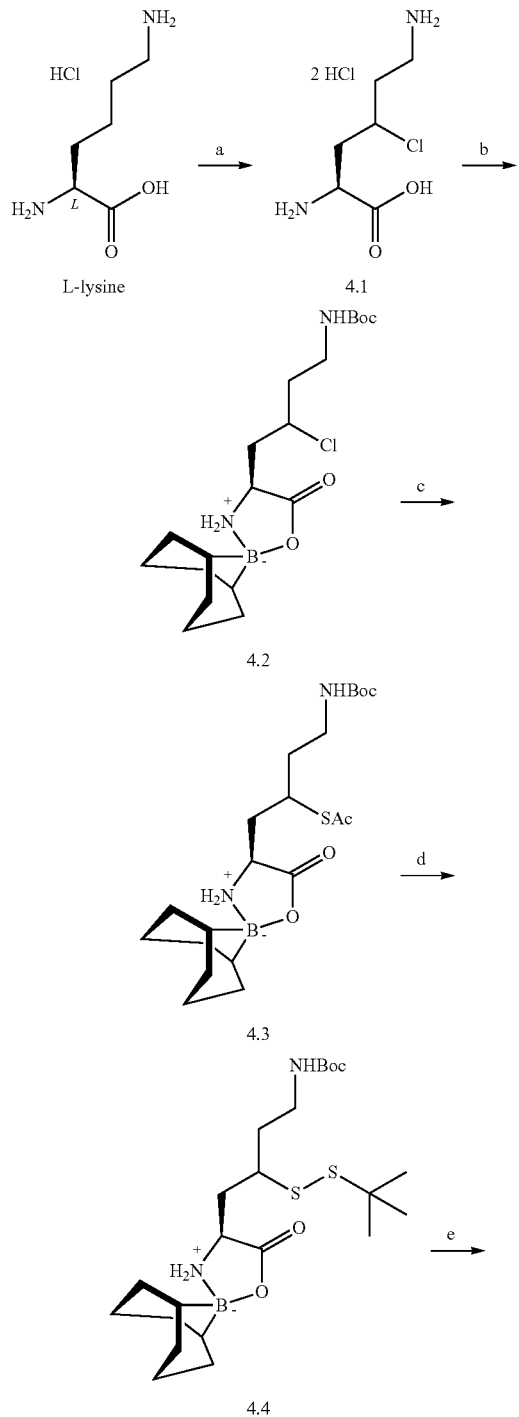

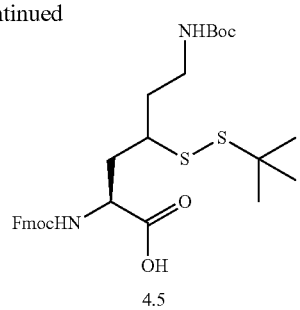

γ-Chloro-L-Lysine Dihydrochloride (4.1).

The synthesis of 4.1 was performed following the literature procedure as was described by Kollonitsch et al. (*J. Am. Chem. Soc.* 1964, 86, 1857) using an experimental setup as is depicted in FIG. 13.

Chlorine was bubbled trough a solution of L(+)-lysine monohydrochloride (150 g, 821 mmol) in HCl (36%) at 70° C. The mixture was irradiated with a medium pressure mercury lamp while stirring. After 2 h the reaction mixture was cooled to 7° C. and a seed crystal was added to induce crystallization. After one hour the resulting crystals were filtered off and the crude product was triturated twice with MeOH. The crystals were collected to afford 4.1 as a white solid. Yield: 12.6 g, 49.7 mmol, 6%. $^1$H-NMR (300 MHz, DMSO-$d_6$) δ 8.81 (br s, αNH$_3$, 3H), 8.43 (br s, εNH$_3$, 3H), 4.48 (m, γCH, 1H), 3.96 (br s, αCH, 1H), 2.94 (m, εCH$_2$, 2H), 2.31 (m, βCH$_2$+δCH, total 3H), 2.04 (m, δCH, 1H). $^{13}$C-NMR (75 MHz, DMSO-$d_6$) δ 169.9 (C=O), 56.6 (γCH), 49.6 (αCH), 38.4 (εCH$_2$), 36.1 (βCH$_2$), 35.1 (δCH$_2$). LC-MS program 3: $R_t$=1.05 min, MS ES+ (amu): 180.94 [M+H]$^+$.

N$^\epsilon$-tert-Butoxycarbonyl-L-lysinato-bicyclononylboron (4.2)

DiPEA (1.75 mL, 10.0 mmol) was added to a stirred solution of 4.1 (1.27 g, 5.0 mmol) in dry MeOH (25 mL). The reaction mixture turned turbid and after 5 minutes 9-BBN (1.40 g, 5.75 mmol) was added. The suspension was heated at 70° C. under nitrogen until a clear solution was obtained (approx. 2 h). LC-MS analysis confirmed complete conversion to the boronated product: $R_t$ 6.73 min (LC-MS program 3), MS ES+ (amu): 300.98 [M+H]$^+$). The solvent was removed in vacuo and the residue was coevaporated twice with DCM. The residue was dissolved in dry THF (25 mL) and DiPEA (1.75 mL, 10.0 mmol) and Boc$_2$O (1.091 g, 5.0 mmol) were added. The reaction mixture was stirred for 3 h before 1N KHSO$_4$ (25 mL) was added. The THF was removed in vacuo, and the remaining aqueous phase was extracted with EtOAc. Subsequently, the organic layer was washed with 1N KHSO$_4$ and brine, dried (Na$_2$SO$_4$) and concentrated. The product was isolated as a white foam by flash column chromatography (EtOAc/n-hexane 3/7→1/1 v/v). Yield: 1.84 g, 4.6 mmol, 92% over 2 steps. $R_f$=0.25 (EtOAc/n-hexane 1/1 v/v); $^1$H-NMR (300 MHz, CDCl$_3$) δ 5.64 (m, αNH, 1H), 5.07-4.87 (m, αNH+εNH, total 2H), 4.31 (m, γCH, 1H), 3.88 (m, αCH, 1H), 3.21 (m, εCH$_2$, 2H), 2.55-2.43 (m, βCH, 1H), 2.19-1.29 (m, βCH+γCH$_2$+6×CH$_2$ borane, total 15H), 1.37 (s, tBu, 9H), 0.54 (br s, 2×CH borane, 2H); $^{13}$C-NMR (75 MHz, CDCl$_3$) δ 173.9 (αC=O), 156.3 (C=O, Boc), 79.8 (C$_q$, tBu), 58.9 (γCH), 53.8 (αCH), 39.5 (βCH$_2$), 38.5 (δCH$_2$), 37.7 (εCH$_2$), 31.8 (CH$_2$ borane), 31.5 (CH$_2$, borane), 31.2 (CH$_2$, borane), 31.1 (CH$_2$, borane), 28.4 (3×CH$_3$, tBu), 24.4 (CH$_2$, borane), 24.1 (CH, borane), 23.8

(CH$_2$, borane), 22.6 (CH, borane). LC-MS program 3: R$_t$=10.74 min, MS ES+ (amu): 401.00 [M+H]$^+$.

N$^\epsilon$-tert-Butoxycarbonyl-4-(S-acetyl)-L-lysinato-bicyclononylboron (4.3)

KSAc (122 mg, 1.07 mmol) was added to a solution of 4.2 (244 mg, 0.61 mmol) in DMF (10 mL). The reaction mixture was stirred at 65° C. for 3 h before the solvent was removed in vacuo. The residue was redissolved in EtOAc, washed with brine, dried (Na$_2$SO$_4$) and concentrated. The product was isolated as a white foam by flash column chromatography (EtOAc/n-hexane 3/7→1/1 v/v). Yield: 229 mg, 0.52 mmol, 85%. R$_f$=0.17 (EtOAc/n-hexane 1/1 v/v); $^1$H-NMR (300 MHz, CDCl$_3$) δ 5.42-5.17 (m, αNH$_2$, 2H), 5.04 (br s, εNH, 1H), 3.68-3.47 (m, αCH+γCH, total 2H), 3.35 (m, εCH, 1H), 3.15-3.01 (m, εCH, 1H), 2.47-2.30 (m, βCH, 1H), 2.38 (s, CH$_3$, SAc, 3H), 2.21-1.36 (m, βCH+δCH$_2$+6×CH$_2$ borane, total 15H), 1.44 (s, 3×CH$_3$, tBu, 9H), 0.64 (br s, CH, borane, 1H), 0.51 (br s, CH, borane, 1H); $^{13}$C-NMR (75 MHz, CDCl$_3$) δ 199.2 (C=O, SAc), 173.5 (αC=O), 157.3 (C=O, Boc), 80.04 (C$_q$, Boc), 53.6 (αCH), 38.4 (γCH), 37.7 (εCH$_2$), 37.1 (δCH$_2$), 36.2 (βCH$_2$), 32.0 (CH$_2$ borane), 31.4 (CH$_2$, borane), 31.3 (CH$_2$, borane), 31.0 (CH$_2$, borane), 30.7 (CH$_3$, SAc), 28.3 (3×CH$_3$, tBu), 24.5 (CH$_2$, borane), 24.0 (CH, borane), 23.9 (CH$_2$, borane), 22.5 (CH, borane). LC-MS program 3: R$_t$=11.14 min, MS ES+ (amu): 440.99 [M+H]$^+$.

N$^\epsilon$-tert-Butoxycarbonyl-4-(tert-butyldisulfanyl)-L-lysinato-bicyclononylboron (4.4)

Thioacetate 4.3 (597 mg, 1.36 mmol) was dissolved in methanol (14 mL) and treated with 1N NaOH (1.36 mL) for 30 min at 0° C. The reaction mixture was carefully neutralized by the addition of equimolar amounts of HOAc and concentrated. The concentrate was redissolved in ethyl acetate and washed with 1N KHSO$_4$ and brine, dried (Na$_2$SO$_4$), and concentrated affording the crude thiol as an oil. In a separate flask, a mixture of MsCl (0.53 mL, 6.80 mmol), 2-methyl-2-propanethiol (0.767 mL, 2.72 mmol) and Et$_3$N (1.90 mL, 13.6 mmol) in DCM (25 mL) was stirred for 30 min before a solution of the crude thiol and Et$_3$N (0.190 mL, 1.36 mmol) in DCM (25 mL) was added. The reaction mixture was stirred for an additional 2 h. Next, 1N KHSO$_4$ (50 mL) was added and the DCM was removed in vacuo. The aqueous residue was extracted with EtOAc and the organic layer was washed with 1N KHSO$_4$ and brine, dried (Na$_2$SO$_4$) and concentrated. The product was isolated as a white foam by flash column chromatography (DCM→EtOAc/DCM 1/1 v/v). Yield: 398 mg, 0.82 mmol, 60% over 2 steps. $^1$H-NMR (300 MHz, CDCl$_3$) δ 5.40 (m, αNH, 1H), 5.16 (m, αNH, 1H), 5.03 (m, εNH, 1H), 4.17-3.99 (m, αCH, 1H), 6.54 (m, εCH, 1H), 3.18-2.99 (m, εCH, 1H), 2.90 (m, γCH, 1H), 2.24 (m, βCH$_2$, 2H), 2.07-1.27 (m, δCH$_2$+6×CH$_2$ borane, total 14H), 1.39 (s, 3×CH$_3$, tBu Boc, 9H), 1.32 (s, 3×CH$_3$, SStBu, 9H), 0.62 (s, 2×CH$_2$, borane, total 2H). $^{13}$C-NMR (75 MHz, CDCl$_3$) δ 173.7 (αC=O), 157.0 (C=O, Boc), 79.9 (C$_q$, tBu Boc), 53.5 (αCH), 48.5 (γCH), 48.4 (C$_q$, SStBu), 37.9 (εCH$_2$), 36.9 (δCH$_2$), 35.8 (βCH$_2$), 32.2 (CH$_2$, borane), 31.3 (CH$_2$, borane), 31.2 (CH$_2$, borane), 30.9 (CH$_2$, borane), 29.9 (3×CH$_3$, SStBu), 28.3 (3×CH$_3$, tBu Boc), 24.3 (CH$_2$, borane), 24.0 (CH, borane), 23.8 (CH$_2$, borane), 22.5 (CH, borane). LC-MS program 3: R$_t$=12.58 min, MS ES+ (amu): 487.00 [M+H]$^+$.

N$^\alpha$-(Fluoren-9-ylmethoxycarbonyl)-N$^\epsilon$-tert-Butoxycarbonyl-4-(tert-butyldisulfanyl)-L-lysinato-bicyclononylboron (4.5)

2N LiOH (7.5 mL) was added to a solution of 4.4 (243 mg, 0.5 mmol) in THF (7.5 mL) and was stirred vigorously for 2 h before the THF was removed in vacuo. The aqueous residue was acidified to pH=4 with 1N HCl, and washed with DCM. The water layer was concentrated to 25 mL and the pH was brought to 8.5 with Et$_3$N. A solution of Fmoc-OSu (252 mg, 0.75 mmol) in MeCN (25 mL) was added. The reaction mixture was stirred at room temperature while the pH was kept between 8 and 8.5. After 30 min the reaction mixture was acidified to pH=3 with 1N HCl and the MeCN was removed in vacuo. 1N KHSO$_4$ (25 mL) was added and the mixture was extracted with EtOAc. The organic layer was washed with 1N KHSO$_4$ and brine, dried (Na$_2$SO$_4$) and concentrated. The product was isolated as a white foam by flash column chromatography (5% MeOH in DCM→>10% MeOH in DCM v/v %). Yield: 63 mg, 0.11 mmol, 21% over 2 steps. $^1$H-NMR (300 MHz, CDCl$_3$) (57.73 (d, J=7.5, 2×Ar—H, Fmoc, total 2H), 7.60 (d, J=6.4, 2×Ar—H, Fmoc, total 2H), 7.41-7.24 (m, 4×Ar—H, Fmoc, total 4H), 6.17 (br s, αNH, 1H), 4.89-4.57 (m, εNH+αCH, total 2H), 4.49-4.13 (m, CH Fmoc+CH$_2$ Fmoc, total 3H), 3.44-3.11 (m, εCH$_2$, 2H), 2.94 (m, γCH, 1H), 2.34-1.60 (m, βCH$_2$+δCH$_2$, total 4H), 1.44 (s, 3×CH$_3$, SStBu, 9H), 1.30 (s, 3×CH$_3$, tBu Boc, 9H). $^{13}$C-NMR (75 MHz, CDCl$_3$) 156.8 (αC=O), 143.9 (C=O), 143.8 (C=O), 141.1 (4×C$_q$, Fmoc), 127.6 (2×Ar CH, Fmoc), 127.1 (2×Ar CH, Fmoc), 125.3 (2×Ar CH, Fmoc), 119.8 (2×Ar CH, Fmoc), 79.8 (C$_q$, tBu Boc), 67.3 (CH$_2$, Fmoc), 52.6 (αCH), 47.7 (C$_q$, SStBu), 47.1 (CH Fmoc), 46.2 (γCH), 37.8 (εCH$_2$), 36.0 (δCH$_2$), 35.3 (βCH$_2$), 30.0 (3×CH$_3$, SStBu), 28.4 (3×CH$_3$, tBu Boc); LC-MS program 3: R$_t$=12.18 min, MS ES+ (amu): 610.89 [M+Na]$^+$.

Example 5

Synthesis of a Galactosyl Bromide Modified Thiolysine Building Block

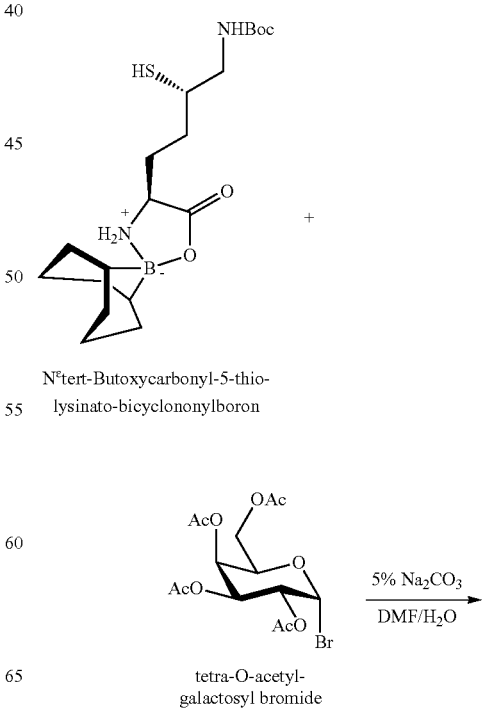

N$^\epsilon$tert-Butoxycarbonyl-5-thio-lysinato-bicyclononylboron tetra-O-acetyl-galactosyl bromide

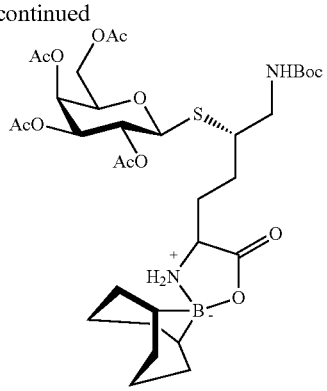

N<sup>ε</sup>tert-Butoxycarbonyl-5-thio-
(β-tetra-O-acetyl-
galactosyl bromide)-
lysinato-bicyclononylboron To a solution of $N^\epsilon$-tert-Butoxycarbonyl-5-thiodysinato-bicyclononylboron (100 mg, 251 μmol) and tetra-O-acetyl-galactosyl bromide (180 mg, 440 μmol, 1.75 eq) in 10 mL of DMF was added 10 mL of 5% $Na_2CO_3$. After stirring the mixture overnight LC-MS analysis showed no presence of thiol and the formation of the thioglycoside. The reaction was diluted with EtOAc, washed with brine and sat. $NaHCO_3$, the organic layer was dried over $MgSO_4$ and concentrated in vacuo to give a residue that was purified by flash column chromatography (n-hexane→EtOAc). Yield: 45 mg, 62 μmol, 25%), yellow oil. LC-MS program 1: $R_t$=11.8 min, MS ES+ (amu): 629.2 [(M-Boc).H]$^+$, 751.25[M.Na]$^+$. (Ref: X. Zhu, K. Pachamuthu, R. R. Schmidt *J. Org. Chem.* 2003, 68, 5641).

Example 6

Synthesis of a Fluorescence Polarization Assay Reagent Via an Fmoc-Thiolysine Building Block

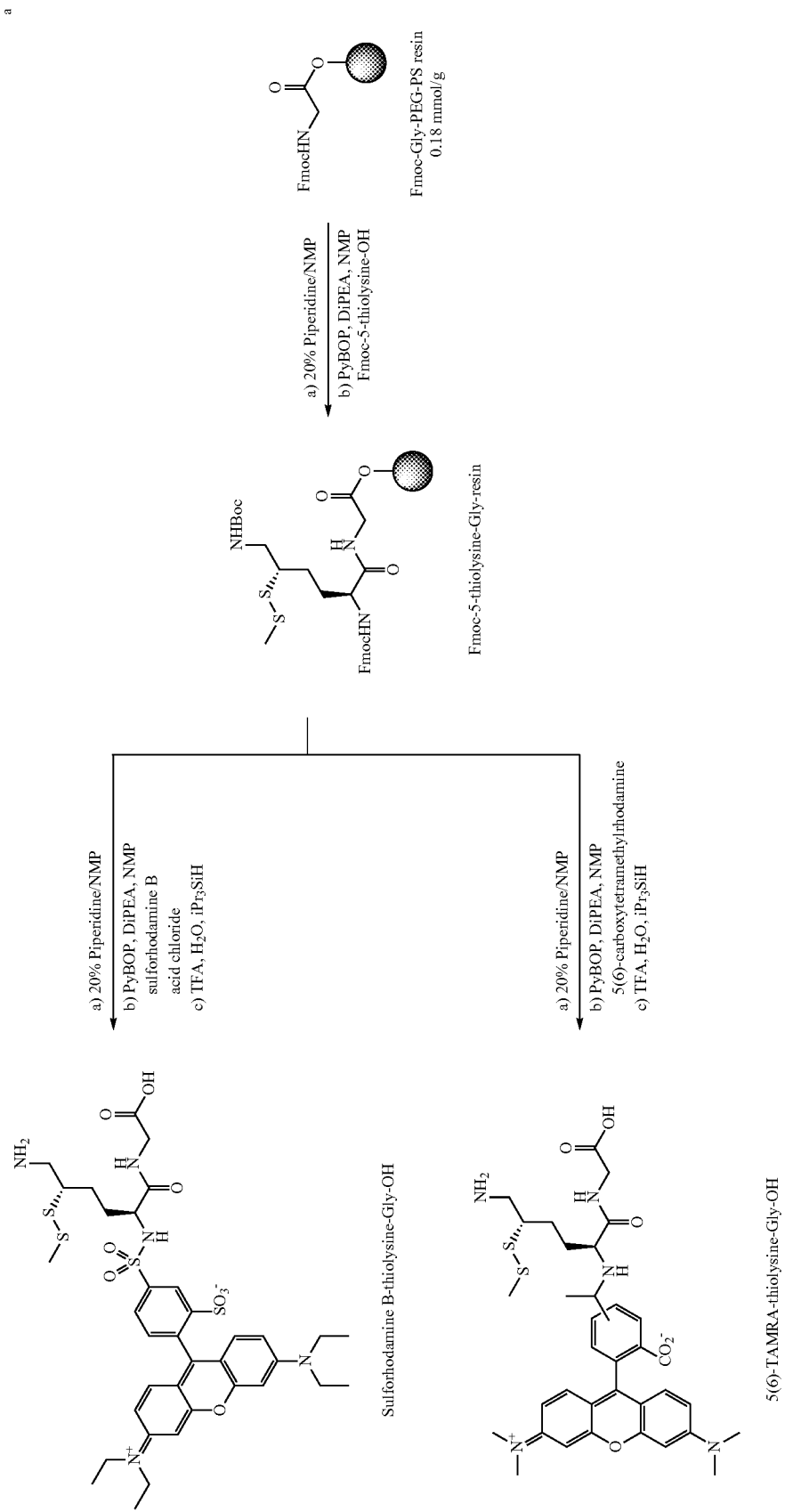

-continued
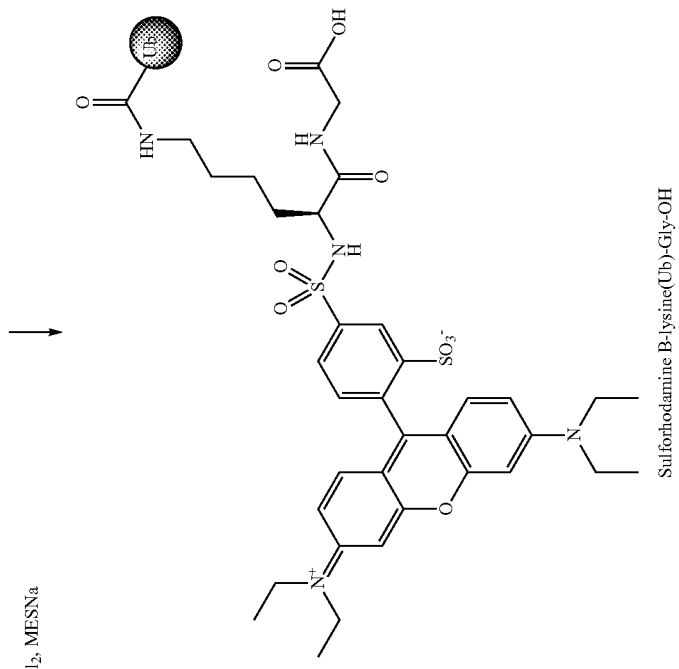
a) Ub, E1, Tris pH 8, 37° C., ATP, MgCl₂, MESNa
b) VA-044, TCEP, 37° C.
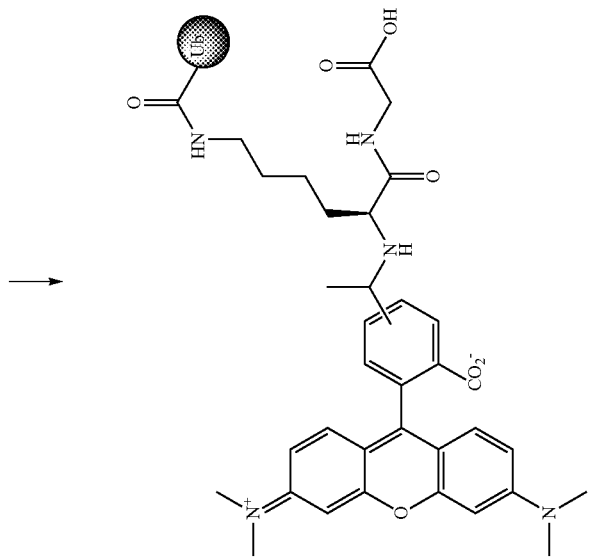

(a): Synthesis of 5(6)-TAMRA-thiolysine-Gly-OH and Sulforhodamine B-thiolysine-Gly-OH conjugates.
(b): E1 mediated synthesis of the fluorescence polarization assay reagents 5(6)-TAMRA-lysine(Ub)-Gly-OH and Sulforhodamine B-lysine(Ub)-Gly-OH (Tirat et al., *Analytical Biochemistry* 2005, 343, 244).

TAMRA-Thiolysine-Gly-OH

To Fmoc-Gly-PEG-PS resin (1.0 g, 0.18 mmol/g) was added piperidine:NMP (20:80 v/v, 5 mL). After shaking for 45 min, the resin was washed with $CH_2Cl_2$. This procedure was repeated, followed by washing with $CH_2Cl_2$/NMP (1/1, v/v) and NMP. To the resin was added $N^\alpha$-(Fluoren-9-yl-methoxycarbonyl)-$N^\epsilon$-tert-Butoxycarbonyl-5S-(methyldisulfanyl)-L-lysine (196.8 mg, 0.36 mmol), PyBOP (206 mg, 0.40 mmol), DiPEA (138 µL, 0.79 mmol) and NMP (5 mL). The resin was shaken overnight at r.t, washed thoroughly with $CH_2Cl_2$/NMP (1/1, v/v) and after a final wash with $Et_2O$, dried under high vacuum. Spectrofotometric analysis of the Fmoc content showed that the thiolysine modified resin had a loading of 18 mmol/g (>99% yield).

Next, the resin (255 mg, 45.9 µmol, 0.18 mmol/g) was treated 3× for 5 minutes with 20% piperidine in NMP (5 mL) and washed extensively with $CH_2Cl_2$/NMP (1/1, v/v). To the deprotected resin was added 5(6)-carboxytetramethylrhodamine (TAMRA, 23.7 mg, 55.1 µmol), PyBOP (28.9 mg, 55.1 µmol), DiPEA (18 µL, 103 µmol) and NMP (5 mL). After shaking overnight, the resin was washed with $CH_2Cl_2$/NMP (1/1, v/v) until the flow-through was colorless. The resin was then treated with TFA/$H_2O$/$Pr_3SiH$ (90/5/5, v/v/v, 4 mL) for 1 h. The solution was eluted and the resin washed with TFA/$CH_2Cl_2$ (1/1, v/v) followed by $CH_2Cl_2$. The flow-through was concentrated and dried under high vacuum, affording TAMRA-thiolysine-Gly-OH (29.3 mg, 92%, 3 steps) as a purple oil. LC-MS program 1: $R_t$ 6.4 min, MS ES+ (amu): 693.46 $[M.H]^+$.

Sulforhodamine B-thiolysine-Gly-OH

To H-Gly-PEG-PS resin (1.0 g, 0.18 mmol/g) was added sulforhodamine B acid chloride (31.9 mg, 55.3 µmol), DiPEA (18 µL, 103 µmol) and $CH_2Cl_2$ (5 mL). After shaking for 15 min, the resin was washed with $CH_2Cl_2$/NMP (1/1, v/v) and treated again with sulforhodamine B acid chloride (13.3 mg, 23.05 µmol) and DiPEA (8 µL, 46.1 µmol). After overnight shaking at rt, the resin was washed with $CH_2Cl_2$/NMP (1/1, v/v) until the flow-through was colorless. Deprotection with TFA was performed as described for the TAMRA conjugate gave the desired Sulforhodamine B-thiolysine-Gly as a purple oil (33.0 mg, 87%). LC-MS program 1: $R_t$=7.5 min, MS ES+ (amu): 821.16 $[M.H]^+$.

Conjugation of Ub to 5(6)-TAMRA- and Sulforhodamine B-thiolysine-Gly

Reaction mixtures Table 2: 100 mM Tris-HCl pH 8.0, 4 mM $MgCl_2$ (4 mM), 50 mM MESNa, 25 µM Ub, 25-500 µM 5(6)TAMRA- or Sulforhodamine B-thiolysine-Gly-OH, 4 mM ATP and 100 nM E1 were incubated at 37° C. for 3 h, fed with an additional 4 µL of ATP and incubated overnight at 37° C. Analysis by LC-MS showed complete ligation in all cases; SDS-PAGE analysis followed by fluorescence imaging of the gel (ProXpress 2D, Perkin Elmer) confirmed conjugation of the dye to Ub.

TABLE 2

Reaction conditions for the ligation of Ub to Sulforhodamine B and 5(6)-TAMRA conjugates

| entry | Tris-HCl | $MgCl_2$ | ATP | MESNa | dye-thiolysine-Gly | Ub | E1 |
|---|---|---|---|---|---|---|---|
| A | 461 µL | 10 µL | 4 µL | 12.5 µL | 1.25 µL (25 µM) | 10.7 µL | 1 µL |
| B | 456 µL | 10 µL | 4 µL | 12.5 µL | 6.25 µL (25 µM) | 10.7 µL | 1 µL |
| C | 449 µL | 10 µL | 4 µL | 12.5 µL | 12.5 µL (25 µM) | 10.7 µL | 1 µL |
| D | 443 µL | 10 µL | 4 µL | 12.5 µL | 18.75 µL (25 µM) | 10.7 µL | 1 µL |
| E | 437 µL | 10 µL | 4 µL | 12.5 µL | 25 µL (25 µM) | 10.7 µL | 1 µL |

Desulfurization of 5(6)-TAMRA- and Sulforhodamine B-thiolysine(Ub)-Gly-OH

To a crude reaction mixture (1.88 mL, final concentration 12.2 µM) was added 0.5 M TCEP (1.88 mL, final concentration 0.24 M) and 100 µL of a 0.2 M VA-044 solution (final concentration 5.2 mM). The reaction was incubated at 37° C. overnight, after which LC-MS analysis showed complete desulfurization of the starting material. The reaction mixture was diluted with 100 mM Tris-HCl pH 8.0 to a total volume of 15 mL and filtered over an Amicon Ultra-15 Centrifugal Filter device (3 kDa cut-off, 30 min at 4000 rpm). After repeating this 6×, a colorless flow-through was obtained indicating that no TAMRA-thiolysine-Gly-OH was present. This was confirmed by LC-MS analysis. The desulfurized product was collected in a total volume of 4.0 mL corresponding to a final concentration of 3.13 µM. LC-MS program 2: $R_t$=9.0 min, MS ES+ (amu): mass found 9157 Da (deconvoluted).

This procedure was identical for the sulforhodamine B conjugate and gave identical results. LC-MS program 2: $R_t$=9.2 min, MS ES+ (amu): mass found 9285 Da (deconvoluted).

The invention claimed is:

1. A lysine compound represented by formula (Ia) or (Ib):

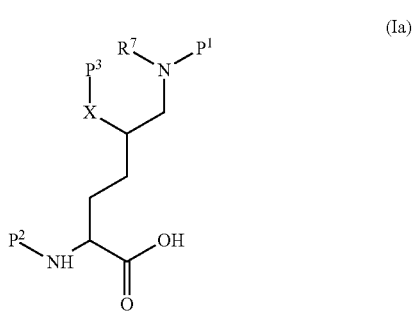

-continued

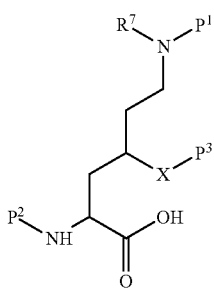
(Ib)

wherein
X is sulfur or selenium;
—P¹ and —P² independently are
  (i) hydrogen, or
  (ii) an amine protecting group,
—P³ is
  (i) hydrogen;
  (ii) —X—R⁶, wherein
    —R⁶ is an optionally substituted branched or straight chain, aliphatic or cyclic alkyl, heteroalkyl, alkenyl or heteroalkenyl group, and
    X is sulfur or selenium;
  (iii) a thiol or selenol protecting group;
  (iv) —R⁵ or
  (v) —C(=O)—R⁵';
  wherein —R⁵ and —C(=O)—R⁵' represent a residue of:
    (a) a covalently bonded peptide, lipid, carbohydrate, or polymer; or
    (b) a covalently bonded functional agent selected from the group consisting of a dye, a probe, a label, a tag, a solubility-modifying agent, an enzyme target, a receptor ligand, an immunomodulatory agent, a co-factor and a cross-linking agent; and
—R⁷ is
  (i) hydrogen, or
  (ii) an optionally substituted branched or straight chain, aliphatic or cyclic alkyl, heteroalkyl, alkenyl or heteroalkenyl moiety;
or an ester, salt, solvate or hydrate of said lysine compound.

2. The lysine compound according to claim 1, or said ester, salt, solvate or hydrate thereof, wherein X is sulfur.

3. A non-naturally occurring peptide represented by formula (IIa) or (IIb):

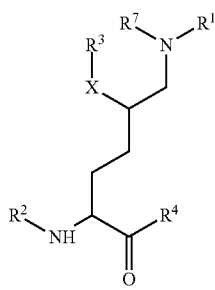
(IIa)

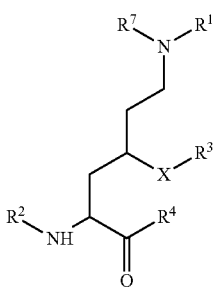
(IIb)

wherein
—R¹ is
  (i) hydrogen;
  (ii) —P¹ as defined in claim 1 or
  (iii) —C(=O)—R⁵';
—R² is
  (i) hydrogen;
  (ii) —P² as defined in claim 1,
  (iii) a C→N polypeptide chain or
  (iv) —C(=O)—R⁵';
—R³ is
  (i) hydrogen;
  (ii) —P³ as defined in claim 1;
  (iii) —R⁵; or
  (iv) —C(=O)—R⁵';
—R⁴ is
  (i) —OH or
  (ii) an N→C polypeptide chain;
X is sulfur or selenium;
wherein —R⁵ and —C(=O)—R⁵' represent a residue of
  (a) a covalently bonded peptide, lipid, carbohydrate, or polymer; or
  (b) a covalently bonded functional agent selected from the group consisting of a dye, a probe, a label, a tag, a solubility-modifying agent, an enzyme target, a receptor ligand, an immunomodulatory agent, a co-factor and a cross-linking agent; and
—R⁷ is
  (i) hydrogen or
  (ii) an optionally substituted branched or straight chain, aliphatic or cyclic alkyl, heteroalkyl, alkenyl or heteroalkenyl group;
with the proviso that at least one of —R² and —R⁴ is a polypeptide chain.

4. The non-naturally occurring peptide according to claim 3, wherein —R⁵ and —C(=O)—R⁵' represent said residue of said covalently bonded functional agent that is selected from the group consisting of a dye, a probe, a label, a tag, a solubility-modifying agent, an enzyme target, a receptor ligand, an immunomodulatory agent, a co-factor and a cross-linking agent.

5. The non-naturally occurring peptide according to claim 3, wherein —R² and —R⁴ include complementary parts of a full amino acid sequence of a naturally occurring polypeptide or protein or functional variant or fragment thereof.

6. The non-naturally occurring peptide according to claim 3, wherein R² and R⁴ represent C→N and N→C polypeptide parts flanking a selected single amino acid residue, in an amino acid sequence of a naturally occurring polypeptide or protein or functional variant or fragment thereof.

7. The non-naturally occurring peptide according to claim 3 formula IIb, wherein —R⁴ is a polypeptide chain and —R² is —P² or hydrogen.

8. A therapeutic or diagnostic agent comprising:
(a) the non-naturally occurring peptide according to claim 3, and
(b) a therapeutically acceptable or diagnostically acceptable carrier or excipient.

9. A method of site-selective and chemoselective modification of a selected polypeptide or protein comprising:
(a) synthesizing or producing said selected polypeptide or protein wherein at least one amino acid residue is a lysine compound represented by formula (Ia) or (Ib)

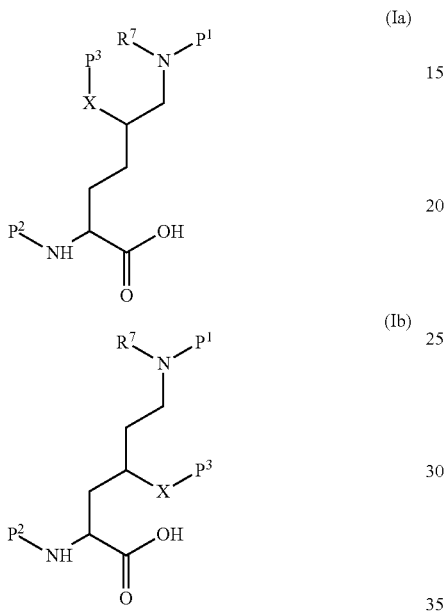

that is incorporated by addition or substitution into said selected protein or polypeptide,
wherein
X is sulfur or selenium;
—$P^1$ and —$P^2$ independently are
(i) hydrogen, or
(ii) an amine protecting group,
—$P^3$ is
(i) hydrogen, or
(ii) a thiol or selenol protecting group; and
—$R^7$ is
(i) hydrogen, or
(ii) an optionally substituted branched or straight chain, aliphatic or cyclic alkyl, heteroalkyl, alkenyl or heteroalkenyl moiety;
(b) removing from the incorporated lysine residue the group represented by —$P^3$ and conjugating a group represented by the formula —$R^5$ or —C(=O)—$R^{5'}$, wherein —$R^5$ and —C(=O)—$R^{5'}$ represent a residue of
(I) a covalently bonded peptide, lipid, carbohydrate, or polymer, or
(II) a covalently bonded functional agent selected from the group consisting of a dye, a probe, a label, a tag, a solubility-modifying agent, an enzyme target, a receptor ligand, an immunomodulatory agent, a cofactor and a cross-linking agent;
wherein the lysine residue is bonded to the sulfur or selenium atom.

10. The method according to claim 9, wherein the —C(=O)—$R^{5'}$ group becomes bonded to the lysine compound to yield a corresponding thio- or selenoester from which X—$P^3$ has been removed, and the method further comprises
(c) intramolecular transfer of said —C(=O)—$R^{5'}$ group to the -ε amino group.

11. The method according to claim 9, wherein the production of said selected polypeptide or protein sequence includes incorporating the lysine using orthogonal tRNA/aminoacyl-tRNA synthetase pairs, wherein said lysine is incorporated in response to a nonsense codon or a four-base codon comprised in a nucleic acid sequence encoding the selected polypeptide or protein.

12. The method according claim 9, wherein said selected polypeptide or protein is a naturally occurring polypeptide or protein or a functional variant or fragment thereof.

13. The method according to claim 9, wherein said selective modification comprises ubiquitination.

14. A method of synthesizing the lysine compound of claim 1, comprising the steps of:
(i) treating
(a) a 4-hydroxylysine or 5-hydroxylysine compound with an organoborane followed by reaction with an amine protecting group, yielding a protected 4-hydroxylsine or 5-hydroxylysine; or
(b) treating a 4-chlorolysine, 5-chlorolysine, 4-bromolysine or 5-bromolysine compound with an organoborane followed by reaction with an amine protecting group, yielding a protected 4-chlorolysine, 5-chlorolysine, 4-bromolysine or 5-bromolysine;
(ii) mesylating the protected 4-hydroxylsine or 5-hydroxylysine obtained in step (i)(a) and subsequently reacting it with a suitable thiocarboxylic acid or selenocarboxylic acid or salt thereof to yield a corresponding thio- or seleno-ester; or reacting the protected 4-chlorolysine, 5-chlorolysine, 4-bromolysine or 5-bromolysine obtained in step (i)(b) with a suitable thiocarboxylic acid or selenocarboxylic acid or salt thereof to yield a corresponding thio- or seleno-ester;
(iii) hydrolyzing the thio- or selenoester obtained in step (ii) with an aqueous solution of an alkali metal hydroxide, yielding the thiol or selenol compound, and subsequently reacting the thiol or selenol compound with an agent that transfers said —$P^3$ group to the thiol or selenol group; and
(iv) removing the protecting organoborane group, and, optionally, subsequently reacting the compound produced in step (iii) with an amine protecting agent, to yield the lysine compound.

15. The lysine compound according to claim 1 wherein the amine protecting group is selected from the group consisting of carbobenzyloxy; p-methoxybenzyl carbonyl; tert-butyloxycarbonyl (Boc); 9-fluorenylmethyloxycarbonyl (Fmoc); benzyl; p-methoxybenzyl; 3,4-dimethoxybenzyl; p-methoxyphenyl; tosyl; sulfonamides; allyloxycarbonyl trityl and methoxytrityl.

16. The lysine compound according to claim 1, wherein the thiol or selenol protecting group is selected from the group consisting of benzyl; 4-methoxybenzyl; trityl; methoxytrityl; t-butyl; t-butylthiol; acetyl; 3-nitro-2-pyridinesulphenyl; acetamidomethyl; methanethiol and 2-nitrobenzyl.

17. The non-naturally occurring peptide according to claim 6, wherein the selected single amino acid residue is a lysine residue.

* * * * *